United States Patent [19]
Copeland et al.

[11] Patent Number: 5,595,707
[45] Date of Patent: Jan. 21, 1997

[54] AUTOMATED BIOLOGICAL REACTION APPARATUS

[75] Inventors: Keith G. Copeland; Thomas M. Grogan; Charles Hassen; William R. Humphreys; Charles D. Lemme; Phillip C. Miller; William L. Richards; Wayne A. Showalter, all of Tucson, Ariz.

[73] Assignee: Ventana Medical Systems, Inc., Tucson, Ariz.

[21] Appl. No.: 352,966

[22] Filed: Dec. 9, 1994

Related U.S. Application Data

[63] Continuation of Ser. No. 924,052, filed as PCT/US91/01149, Feb. 28, 1991 published as WO91/13335, Sep. 5, 1991, abandoned, which is a continuation-in-part of Ser. No. 488,601, Mar. 2, 1990, abandoned.

[51] Int. Cl.$^6$ .................................................. G01N 35/10
[52] U.S. Cl. ............................. 422/64; 422/63; 422/66; 422/67; 436/43; 436/46; 436/48; 436/49; 436/180
[58] Field of Search ......................... 422/63–67, 104; 436/43, 44, 46, 47, 48, 49, 50, 174, 180, 807, 809, 810

[56] References Cited

U.S. PATENT DOCUMENTS

| Re. 30,730 | 9/1981 | Duff | 422/64 |
|---|---|---|---|
| 3,772,154 | 11/1973 | Isenberg et al. | 435/291 X |
| 4,113,437 | 9/1978 | Duff et al. | 422/63 |
| 4,200,607 | 4/1980 | Suzuki | 422/64 |
| 4,298,571 | 11/1981 | Difulvio et al. | 422/65 |
| 4,346,056 | 8/1982 | Sakurada | 422/64 |
| 4,406,547 | 9/1983 | Aihara | 356/414 |
| 4,447,395 | 5/1984 | Englar et al. | 422/63 |
| 4,455,280 | 6/1984 | Shinohara et al. | 422/63 |
| 4,567,748 | 2/1986 | Klass et al. | 422/50 |
| 4,585,622 | 4/1986 | Bowe et al. | 422/50 |
| 4,656,006 | 4/1987 | Assmann et al. | 422/64 X |
| 4,708,886 | 11/1987 | Nelson | 422/72 |
| 4,764,342 | 8/1988 | Kelln et al. | 422/72 |
| 4,774,055 | 9/1988 | Wakatake et al. | 422/100 |

(List continued on next page.)

FOREIGN PATENT DOCUMENTS

| WO87/00086 | 1/1987 | European Pat. Off. . |
| WO88/02865 | 4/1988 | European Pat. Off. . |

OTHER PUBLICATIONS

Stark et al., "An automatic device for immunocytochemistry", 107 (1988) pp. 89–92.
Catalog, "Fisher 86," Allied Fisher Scientific, pp. 93–99.

*Primary Examiner*—Long V. Le
*Attorney, Agent, or Firm*—Skjerven, Morrill, MacPherson, Franklin & Friel; Laura Terlizzi; Philip J. McKay

[57] ABSTRACT

An automated immunostaining apparatus having a reagent application zone and a reagent supply zone. The apparatus has a carousel slide support supporting a plurality of slide supports thereon, and drive means engaging the carousel slide support for consecutively positioning each of a plurality of slide supports in the reagent application zone. The apparatus also has a carousel reagent support having a plurality of reagent container supports thereon, and drive means engaging the carousel for rotating the carousel and positioning a preselected reagent container support in the reagent supply zone. The apparatus also has a reagent delivery actuator means positioned for engaging a reagent container positioned on a container support in the reagent delivery zone and initiating reagent delivery from the reagent container to a slide supported on a slide support in the reagent receiving zone.

29 Claims, 37 Drawing Sheets

U.S. PATENT DOCUMENTS

| | | | |
|---|---|---|---|
| 4,781,891 | 11/1988 | Galle et al. | 422/64 |
| 4,795,710 | 1/1989 | Muszak et al. | 435/287 |
| 4,815,978 | 3/1989 | Mazza et al. | 435/4 |
| 4,844,868 | 7/1989 | Rokugawa | 422/64 |
| 4,849,177 | 7/1989 | Jordan | 422/64 |
| 4,865,811 | 9/1989 | Newton et al. | 422/81 |
| 4,900,513 | 2/1990 | Barker et al. | 422/64 |
| 4,919,887 | 4/1990 | Wakatake | 436/43 |
| 4,933,147 | 6/1990 | Hollar et al. | 422/64 |
| 4,943,415 | 7/1990 | Przybylowicz | 422/56 |
| 4,961,906 | 10/1990 | Andersen et al. | 422/102 |
| 4,965,049 | 10/1990 | Lilling et al. | 422/68.1 |
| 4,988,482 | 1/1991 | Weston | 422/100 |
| 5,051,238 | 9/1991 | Umetsu et al. | 422/64 |
| 5,059,393 | 10/1991 | Quenin et al. | 422/64 |
| 5,075,079 | 12/1991 | Kerr et al. | 422/64 |
| 5,081,038 | 1/1992 | Sugaya et al. | 422/64 X |
| 5,102,624 | 4/1992 | Muraishi | 422/64 |
| 5,106,583 | 4/1992 | Raysberg et al. | 422/64 |
| 5,232,644 | 8/1993 | Krawzak et al. | 422/64 |
| 5,250,262 | 10/1993 | Heidt et al. | 422/64 |
| 5,316,728 | 5/1994 | Hayashi et al. | 422/70 |

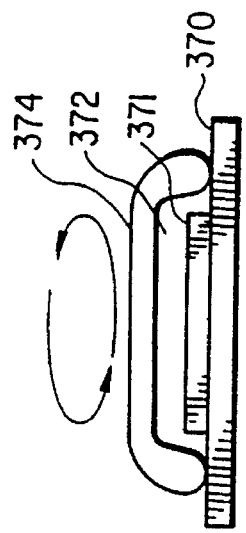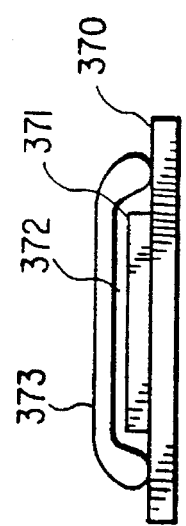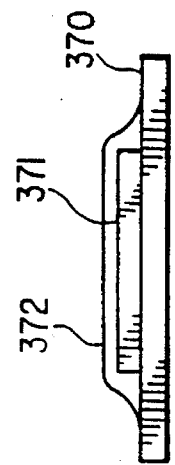

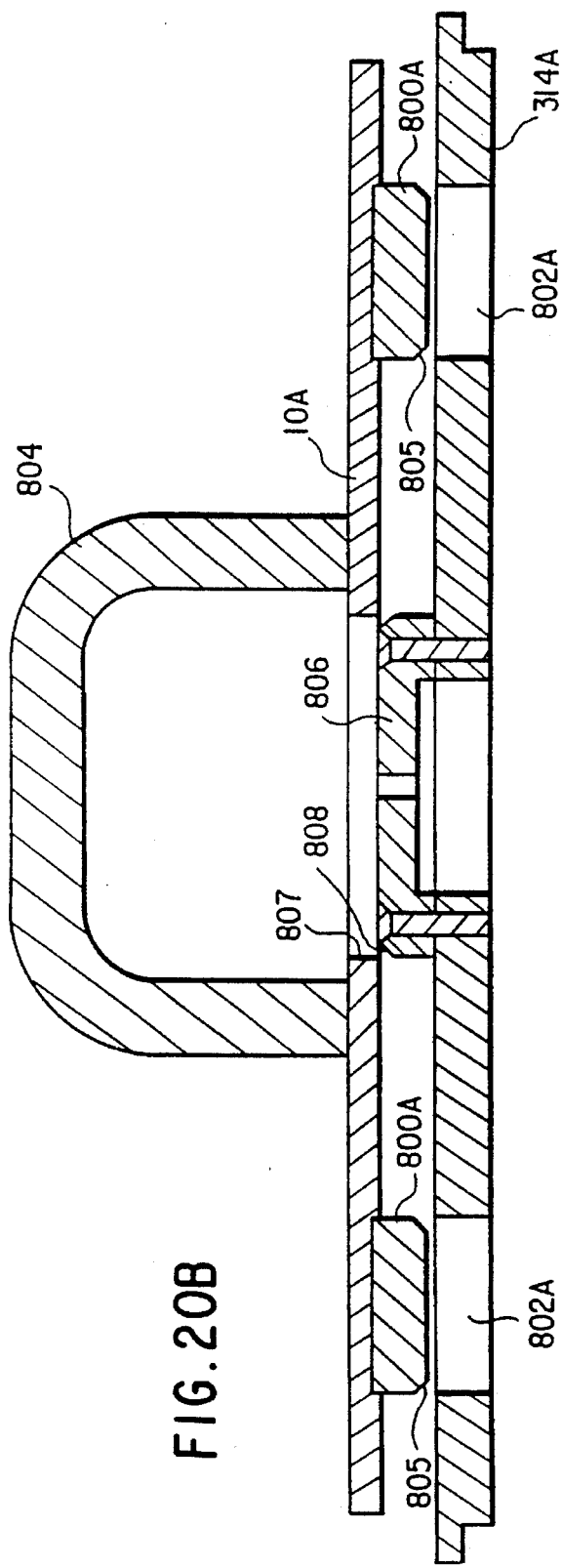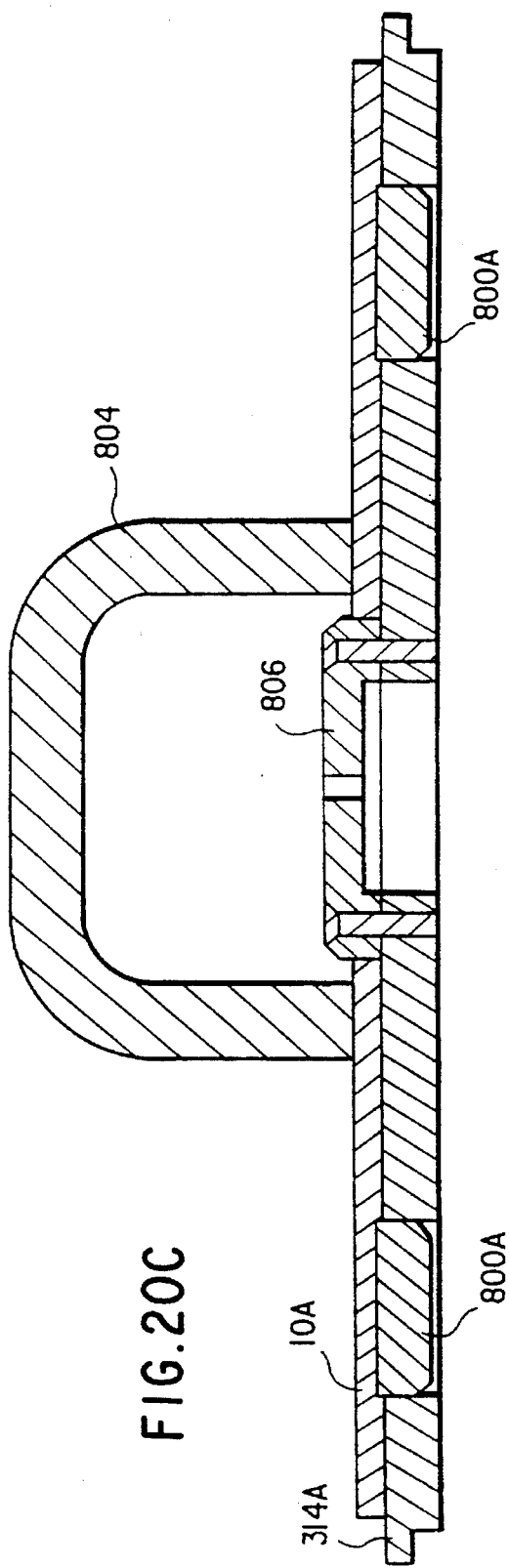

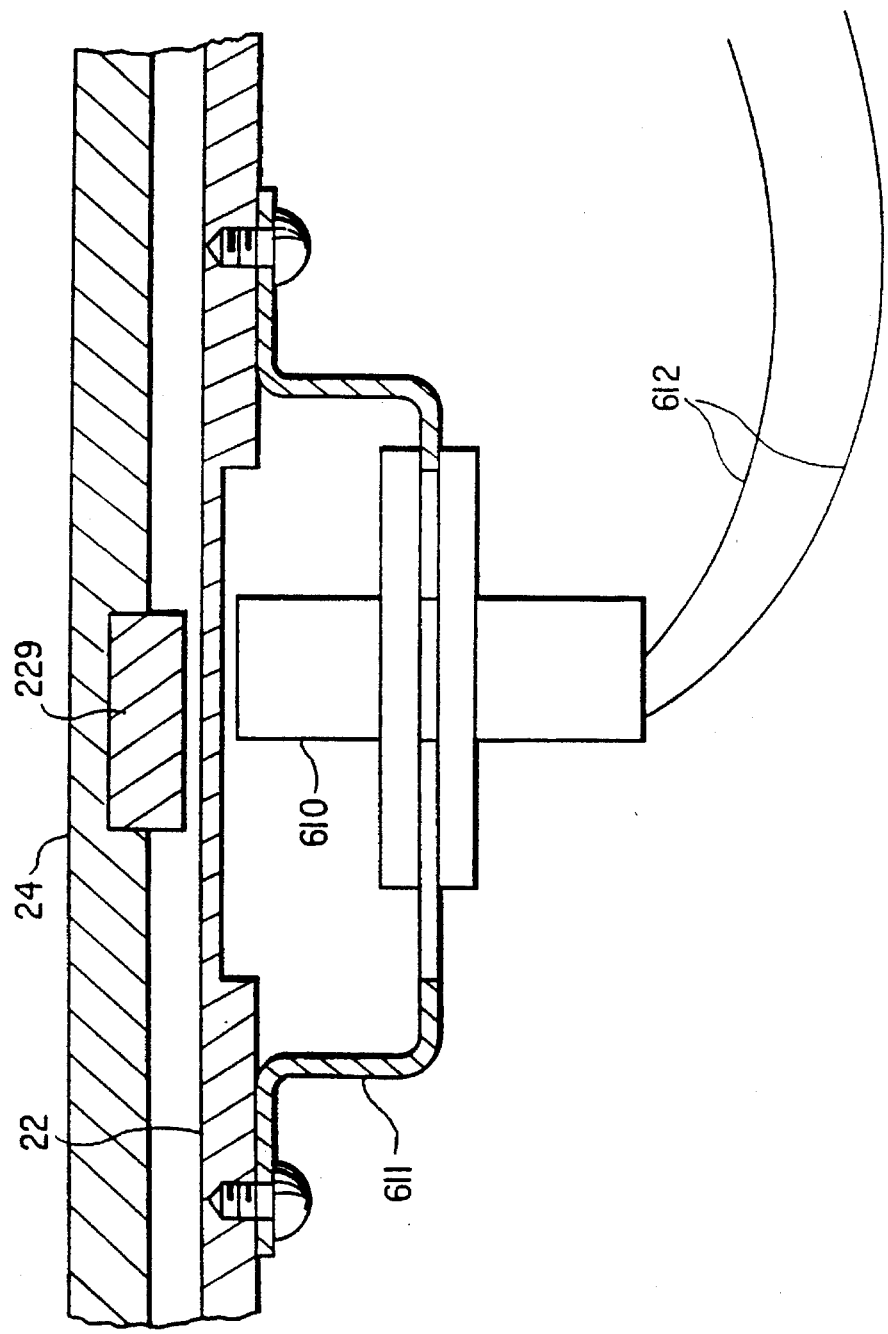

AUTOMATED BIOLOGICAL REACTION APPARATUS

This application is a continuation of U.S. application Ser. No. 07/924,052 (now abandoned), filed Aug. 31, 1992, which is the U.S. national phase application of International Application No. PCT/US91/01149, filed Feb. 28, 1991, published as WO91/13335, Sep. 5, 1991 which is a continuation-in-part application of U.S. patent application Ser. No. 07/488,601 (now abandoned), filed Mar. 2, 1990.

TECHNICAL FIELD

This invention relates an improved biological reaction platform which can be used for a wide variety of assays, for example, automatic immunostaining of tissue sections, in situ DNA analysis, immunoassays such as ELISA, and the like. The automatic device of this invention can be used to process a large number of samples such as tissue sections mounted on slide surfaces using agents and protocols preselected by the operator, while maintaining the slide surfaces in a substantially horizontal plane throughout the incubation cycles.

BACKGROUND ART

Immunostaining and in situ DNA analysis are useful tools in histological diagnosis and the study of tissue morphology. Immunostaining relies on the specific binding affinity of antibodies with epitopes in tissue samples, and the increasing availability of antibodies which bind specifically with unique epitopes present only in certain types of diseased cellular tissue. Immunostaining requires a series of treatment steps conducted on a tissue section mounted on a glass slide to highlight by selective staining certain morphological indicators of disease states. Typical steps include pretreatment of the tissue section to reduce non-specific binding, antibody treatment and incubation, enzyme labeled secondary antibody treatment and incubation, substrate reaction with the enzyme to produce a fluorophore or chromophore highlighting areas of the tissue section having epitopes binding with the antibody, counterstaining, and the like. Each of these steps is separated by multiple rinse steps to remove unreacted residual reagent from the prior step. Incubations are conducted at elevated temperatures, usually around 40° C., and the tissue must be continuously protected from dehydration. In situ DNA analysis relies upon the specific binding affinity of probes with unique nucleotide sequences in cell or tissue samples and similarly involves a series of process steps, with a variety of reagents and process temperature requirements.

Automated systems have been explored to introduce cost savings, uniformity of slide preparation, and reduction of procedural human errors. Stross, W. et al, *J.Clin.Pathol.* 42:106–112 (1989) describes a system comprising a series of baths positioned under the circumference of a circular, rotatable disc from which slide trays are suspended. The disc is lifted to lift slide trays from their baths, turned to position the slide trays above the next consecutive bath, and lowered to immerse the slide trays in the baths. This operation can be automated with suitable timers and switches. This system exposes each of the slides to the same treatment and relies on dipping for application of reactants and rinsing.

Stark, E. et al, *J.Immunol.Methods.* 107:89–92 (1988) describes a microprocessor controlled system including a revolving table or carousel supporting radially positioned slides. A stepper motor rotates the table, placing each slide under one of the stationary syringes positioned above the slides. A predetermined volume of liquid, determined by a dial, is delivered to a slide from each syringe. Microprocessor controls are provided.

Cosgrove, R. et al, *ACL.* pp 23–27 (December, 1989) describe an immunostaining apparatus for auto-pipetting reagents into a slide well from a carousel holding up to 18 reagent vials. Below each well, a coverplate spaced from the surface of each slide provides cover and defines a reagent flow channel. The slides are suspended at a steep angle. Reagent from the well flows downward over the slide surface. A row of slides ale suspended for sequential treatment. Washing is accomplished by a 3 to 4 minute continuous running wash over the sample, yielding an estimated 20:1 wash/reagent ratio.

Brigati, D. et al, *J.Histotechnology* 11:165–183 (1988) and Unger, E., Brigati, D. et al, et al, *J.Histotechnology.* 11:253–258 (1988) describe the Fisher automated work station using capillary gap technology. A coverplate is placed over the slide, forming a capillary gap. Liquid is introduced into the capillary gap by placing the lower edge of the plate-slide pair in a liquid. Liquid is removed by placing the lower edge of the plate-slide pair on a blotter. The system is further described in U.S. Pat. Nos. 4,777,020, 4,798,706 and 4,801,431. The previously known devices are limited in their performance and unable to satisfy the needs for automated, high precision immunohistology.

It is an object of this invention to provide a device which provides more rapid, reliable and more reproducible results than standard methods; can perform any standard immunochemical assay including assays relying on immunofluorescence, indirect immunoassay procedures, peroxidase anti-peroxidase methods, or avidin-biotin technology; performs all steps of the immunohistochemical assay irrespective of complexity or their order, at the time and temperature, and in the environment needed; and is cost effective in terms of equipment, reagent and labor costs.

DISCLOSURE OF THE INVENTION

The automated biological processing apparatus of this invention comprises a reagent carousel cooperating with a sample support carousel to apply a sequence of preselected reagents to each of the samples with interposed mixing, incubating, and rinsing steps cooperating therewith. The slide support carousel has a plurality of slide supports thereon and drive means engaging the slide support carousel for consecutively positioning each of a plurality of slide supports in a reagent receiving zone. The reagent carousel has a plurality of reagent container supports thereon and drive means engaging the reagent carousel for rotating this carousel and positioning a preselected reagent container support and associated reagent container in a reagent supply zone. The apparatus has a reagent delivery actuator means positioned for engaging a reagent container positioned on a container support in the reagent supply zone and initiating reagent delivery from the reagent container to a slide supported on a slide support in the reagent receiving zone.

The apparatus preferably has bar code readers positioned to read bar codes on the sample containers or slides and on the reagent containers. Each of the carousels have homing systems containing a detectable component and a proximity detector therefor for indexing the position of the reagent containers and slides.

One particular advantageous feature of the present invention is that by employing a computer control arrangement to control the positioning of the reagent and slide support carousel, different reagent treatments can be individually performed for each of the various tissue samples by appropriate programming of the apparatus. Additionally, the provision of the bar code readers permits tracking of each of the tissue samples as well as a record of the reagents applied thereto.

The apparatus preferably has a heating chamber means surrounding the slide support carousel for heating slides supported thereon to a predetermined temperature. The heating chamber means includes a hot gas manifold having a plurality of hot gas outlets positioned above the slide supports. The heating chamber means includes a temperature sensor and a hot gas control means connected to the temperature sensor for increasing heat supplied to gas flowing through the manifold and for increasing the hot gas flow rate if further heat is required to maintain the heating chamber at a preselected temperature. The temperature sensor is a thermistor, the tip thereof being enclosed in a heat sensitivity reducing jacket. The hot gas control system includes two heating components with separate controls and a speed control for the hot gas fan.

The drive means engaging the slide support carousel is also a means for consecutively positioning each of a plurality of slide supports at a rinse zone, an evaporation control liquid and reagent receiving zone, a vortex mixing zone including vortex mixing means, and an incubation zone formed by the heating chamber means.

According to a first embodiment of the rinse zone, rinse spray means are positioned adjacent to the rinse zone for applying pulses of rinse liquid to the surface of each of the slides positioned in the rinse zone. The apparatus slide supports are, according to this first embodiment of the rinse zone, pivotally mounted for pivotal motion from a horizontal slide incubation position to a tilted slide draining position following each pulse of rinse liquid.

According to a second embodiment of the rinse zone, first and second rinse spray means are respectively positioned only at the beginning and end of the rinse zone, so as to be spaced from one another. The first rinse spray means deposits a layer of rinse liquid onto a slide upon entering the rinse zone and the second spray means, after a predetermined waiting period, uses pulsed streams of rinse liquid, alternately directed at the longitudinal edges of the slides, to knock the previously deposited layer of rinse liquid off of the slide as the slide exits the rinse zone. According to this second embodiment of the rinse zone, the apparatus slide supports are stationary, a jet drain being provided at, for example, the end of the rinse zone, which directs a stream of fluid, such as, for example, air or the like, over the slide to drain any remaining rinse liquid off of the slide surface.

The apparatus preferably has a volumetric pump means, and a reagent delivery actuator means positioned for activating the volumetric pump means, thereby effecting delivery of reagent from a reagent container by the volumetric pump to the reagent delivery zone. An evaporation inhibitor liquid application means is positioned adjacent the reagent delivery zone.

Vortex agitation means are positioned adjacent the agitation zone for stirring reactants on a slide supported in the vortex agitation zone.

The pivoting slide support has distal and proximal ends, the distal end having raised terminal and lateral distal guide tabs with guide termini. The proximal end has first and second lateral guide tabs with opposed slide engaging surfaces for engaging and holding the lateral edges of a slide. The guide termini are lower than the upper slide surface plane. In this embodiment of the slide support, the slide support surface is tipped or pivoted by a tipper to drain rinse liquid from the surface of the slide.

The stationary slide support has a slide support platform at a proximal end and a slide support post at a distal end thereof. The distal end also has raised lateral distal guide tabs with guide termini between which a slide is positioned. The slide support platform at the proximal end has a guide edge and a slide clamping arrangement for clamping a slide to the support platform without interfering with the reading operation of the bar code reader. The distal guide termini are lower than the upper slide surface plane to prevent wick-off of liquid on the slide surface. In this embodiment, rinse liquid is drained from the surface of the slide employing a jet drain which directs a stream of fluid, i.e., gas or liquid, over the slide surface.

An improved biochemical method of this invention with increased sample dehydration protection comprises carrying out a biochemical reaction under a layer of evaporation inhibiting liquid. The improvement comprises (a) covering the sample with an aqueous surface layer by applying an aqueous solution to a planar support surface adjacent a biological sample mounted thereon; and (b) covering the aqueous surface layer with an evaporation inhibiting liquid layer by applying the evaporation inhibiting liquid to the planar support surface adjacent the biological sample in an amount sufficient to form a continuous layer of evaporation inhibiting liquid over the sample. The evaporation inhibiting liquid is substantially water-insoluble, substantially water-immiscible and substantially non-viscous; has a specific gravity less than water, and a boiling point above 50° C.; and is devoid of chemical characteristics which would significantly interfere with biochemical reactions carried out on the sample. The biological sample can then be optionally treated (c) with an aqueous reagent solution by applying the reagent solution to the planar support surface adjacent the biological sample. The reagent solution flows to the biological sample under the evaporation inhibiting liquid layer, and the sample is continuously protected from dehydration by the evaporation inhibiting layer.

In another aspect of this invention, the reagent solution is stirred on the surface of the biological sample by applying at least one gas stream to an area of the surface of the evaporation inhibiting liquid layer between the center of the evaporation inhibiting layer and the edge of the planar support surface, the gas stream having a central axis forming an acute angle with the planar support surface. According to one embodiment of the present invention, the reagent solution is preferable stirred by a vortex formed by applying two off-center gas streams, flowing in opposite directions, to the surface of the evaporation inhibiting liquid layer. According to a further embodiment of the present invention, the reagent solution is stirred by a vortex formed by applying a single gas stream along a longitudinal edge of the slide, the gas stream originating from the distal edge of the slide.

BRIEF DESCRIPTION OF THE DRAWINGS

FIG. 18 is a schematic representational cross-sectional view of a slide following the rinse liquid, evaporation inhibitor and reagent application steps.

FIGS. 20B–20C are side sectional views of a further embodiment of the reagent container support tray.

FIG. 21 is a fragmentary cross-sectional view taken along the line D—D in FIG. 11 showing the slide carousel metal proximity sensor indexing system of this invention.

BEST MODE FOR CARRYING OUT THE INVENTION

The automated immunostaining apparatus of this invention performs all steps of immunohistochemical and in situ DNA assays irrespective of complexity or their order, at the time and temperature, and in the environment needed. Specially prepared slides containing a bar code identifier and a mounted tissue section are placed in special support on a carousel, subjected to a preprogrammed sequence of reactions, and are removed from the carousel, ready for cover-slipping and histological examination. For purposes of clarity of the following description of the apparatus of this invention and not by way of limitation, the apparatus will be described in terms of immunohistochemical processes.

Figure 1:
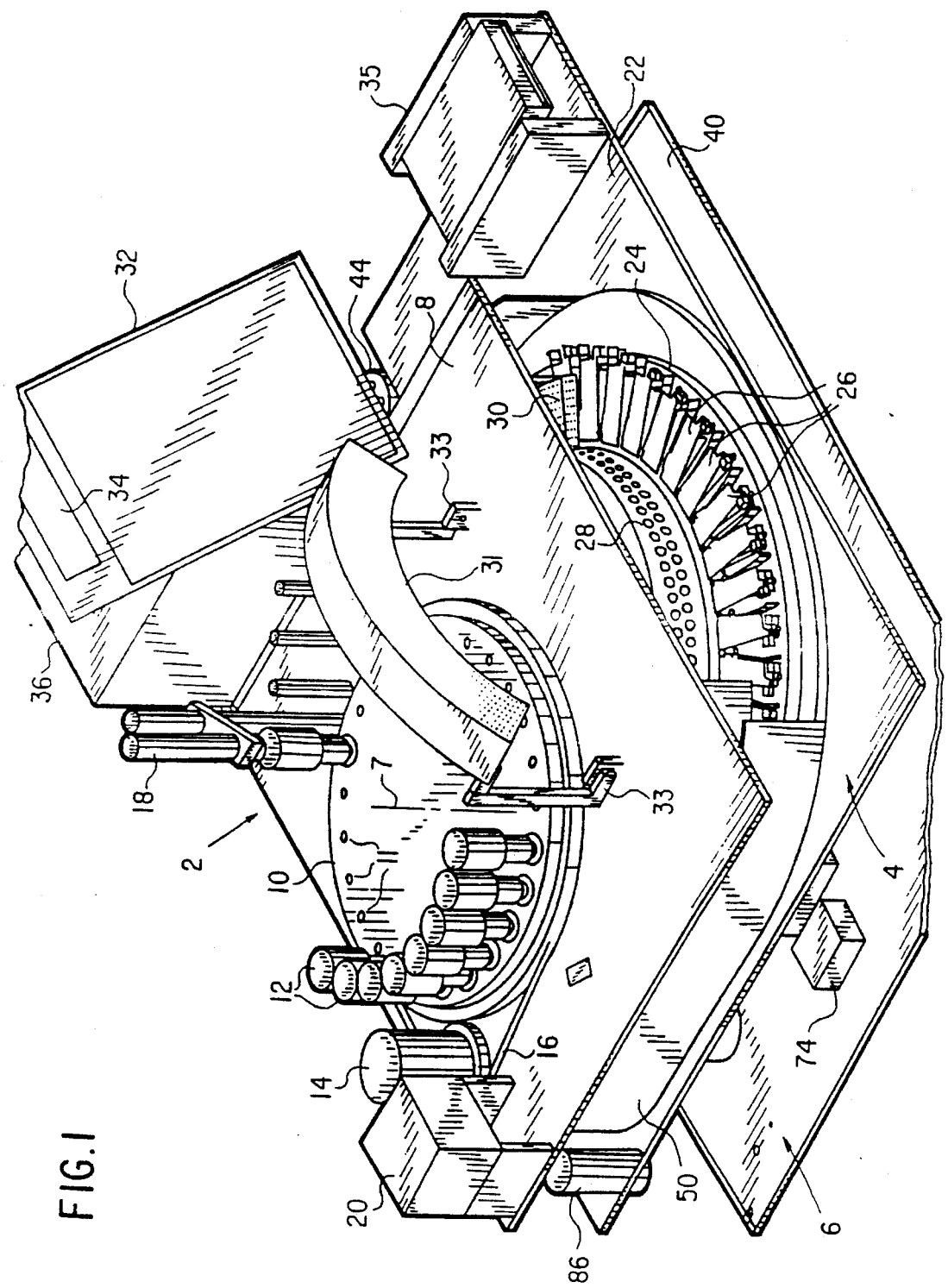
FIG. 1 is a left front, isometric view of the automated immunostaining apparatus according to a first embodiment of this invention which employs a tipper rinse method, with the cabinet shell removed.

FIG. 1 is a front right, isometric view of the automated immunostaining apparatus of this invention, with the cabinet shell removed. Liquid and air supply tubing and electrical wiring connecting the respective components are conventional, well known in the art, and are omitted from the drawings for purposes of clarity. The apparatus has an upper section 2, intermediate section 4 and lower section 6. In the upper section 2, reagent bottle support carousel 10 is mounted for rotation about its central axis 7 on upper support plate 8. Reagent bottles 12 required for the immunohistochemical reactions to be conducted during slide treatment cycle are supported by the carousel 10, mounted in reagent bottle receptors 11. These receptors 11 are configured to receive volumetric pump outlet tube 307, shown in detail in FIG. 15. The receptors 11 are preferably equally spaced in a circular pattern axially concentric with the carousel axis 7. The number of receptors 11 provided should be sufficient to accommodate the number of different reagent bottles 12 required for a cycle or series of cycles. Twenty-five receptors 11 are shown, but the number can be smaller or greater, and the diameter of the carousel 10 can be increased to accept a larger number of reagent bottles 12. The carousel 10 is rotated by the stepper motor 14 drive belt 16 to a position placing a selected reagent bottle 12 in the reagent deliver position under the air cylinder reagent delivery actuator 18 over a slide to be treated with reagent. Reagent tray motor driver 20 is connected to stepper motor 14.

The intermediate section 4 comprises support plate 22 upon which the slide support carousel 24 is rotatably mounted. The carousel 24 supports slide supports 26. Heated air supply chamber 28 communicates with the heated air supply manifold 30 supported on the underside of plate 8 and lid heated air supply manifold 31 mounted on the upper plate 8 by hinged supports 33. The support plate 22 also supports the conventional computer board 32, LCD display 34, disk drive 35 and computer 36 used to operate the apparatus. Air pressure regulator 38, as best seen in FIG. 2, regulates the pressure of air delivered to the evaporation inhibitor and rinse liquid delivery systems described in FIG. 22.

The lower section 6 includes support plate 40 upon which are supported accessories such as power supply filter 42 and hot water supply 44.

Figure 2:
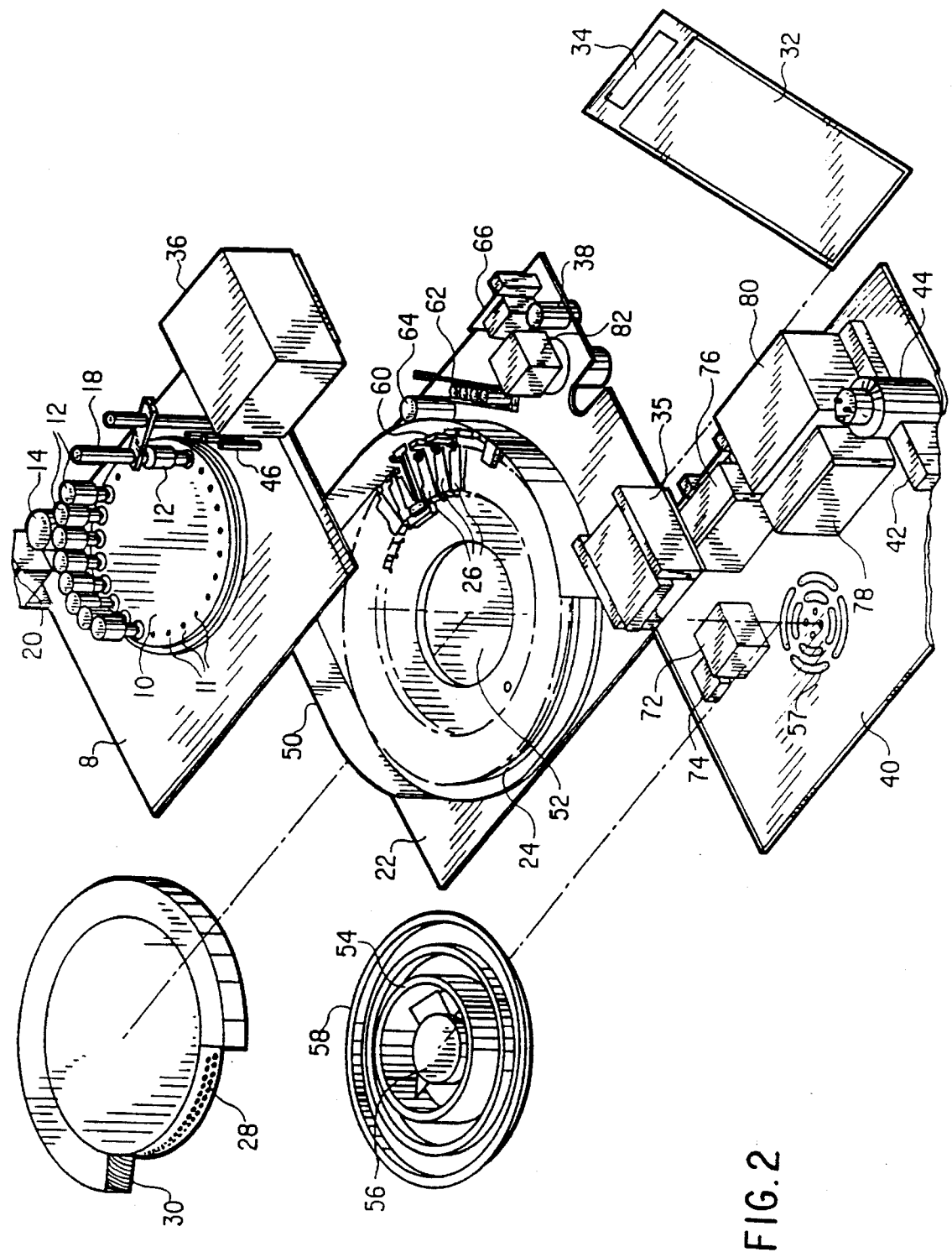
FIG. 2 is an exploded right front isometric view of the apparatus shown in FIG. 1.
Figure 3:
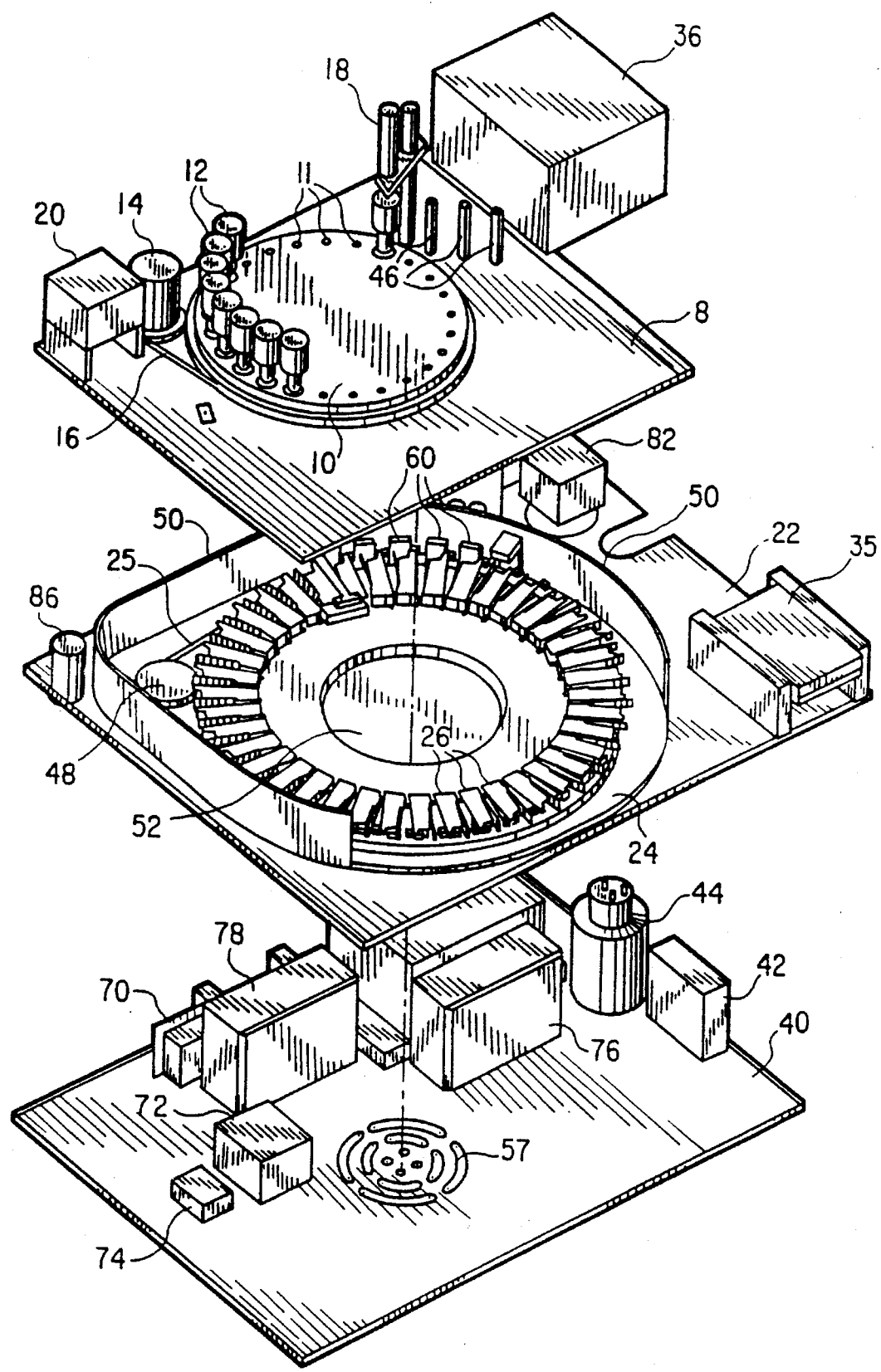
FIG. 3 is a partial exploded left front isometric view of the apparatus shown in FIG. 1.
Figure 4:
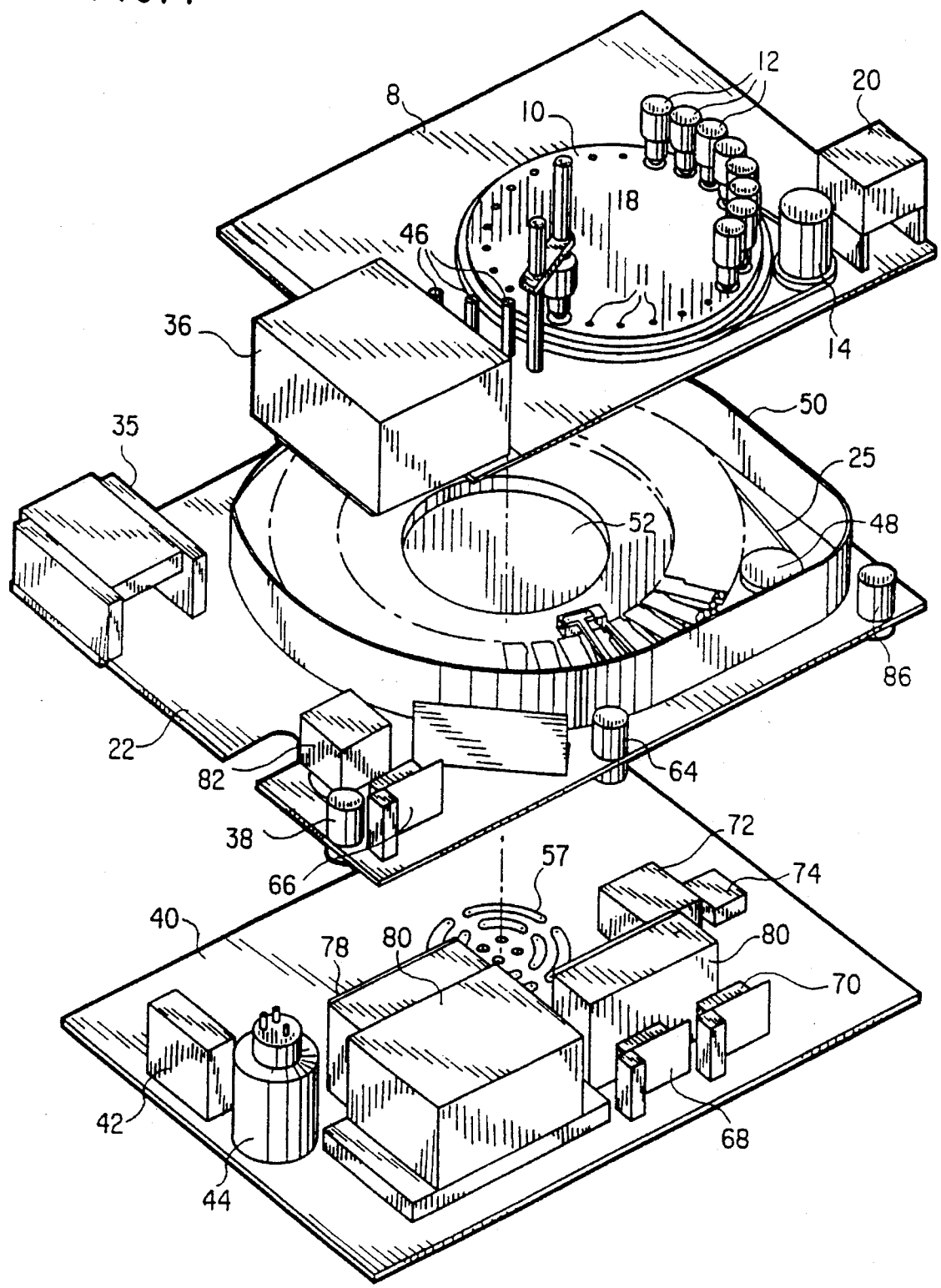
FIG. 4 is a partial exploded right rear isometric view of the apparatus shown in FIG. 1.

FIG. 2, FIG. 3 and FIG. 4 are exploded right front, left front and right rear isometric views of the apparatus shown in FIG. 1. Tipper air cylinders 46 are positioned on support plate 8. These cylinders are aligned to actuate a tipper cam surface 148 against a slide support tab surface 112 shown in detail in FIGS. 8, 9 and 10.

In the intermediate section 4, the stepper motor 48 rotates the slide support carousel 24, engaging drive belt 25 (FIGS. 3 and 4) engaging the perimeter of the slide support carousel 24. Splash guard 50 is a wall which surrounds the sides, back and part of the front of the carousel 24, defines the heating zone and contains the liquid spray and droplets produced in the processing. It extends upward from the intermediate plate 22 to a position adjacent the upper plate 8, leaving an air flow gap between the upper edge of the splash guard 50 and the underside of the plate 8. Mounted on the underside of upper support plate 8 above the carousel 24 and within the perimeter of the splash guard 50 is the heated gas supply manifold 30 (FIG. 2). Heated air is directed downward and over the slide supports 26 by holes 336 (FIG. 15) in the manifold 30. The heated air then passes upward over the top of the splash guard 50 and exits the device. Extending upward through central opening 52 of carousel 24 into the heated air supply chamber 28 is the fan shroud 54 and axially positioned fan 56. The fan 56 is positioned over air vents 57 in the bottom plate 22. The annular waste liquid sump 58 surrounds the shroud 54, below liquid outlet ports 292 (FIG. 14), and is supported on the bottom of plate 22. The waste reagent and rinse liquids are collected in the sump and passed to a drain through an outlet tube in the sump bottom (not shown).

Rinse and liquid coverslip spray blocks 60 are supplied with liquid through conventional solenoid valves 62.

Figure 15:
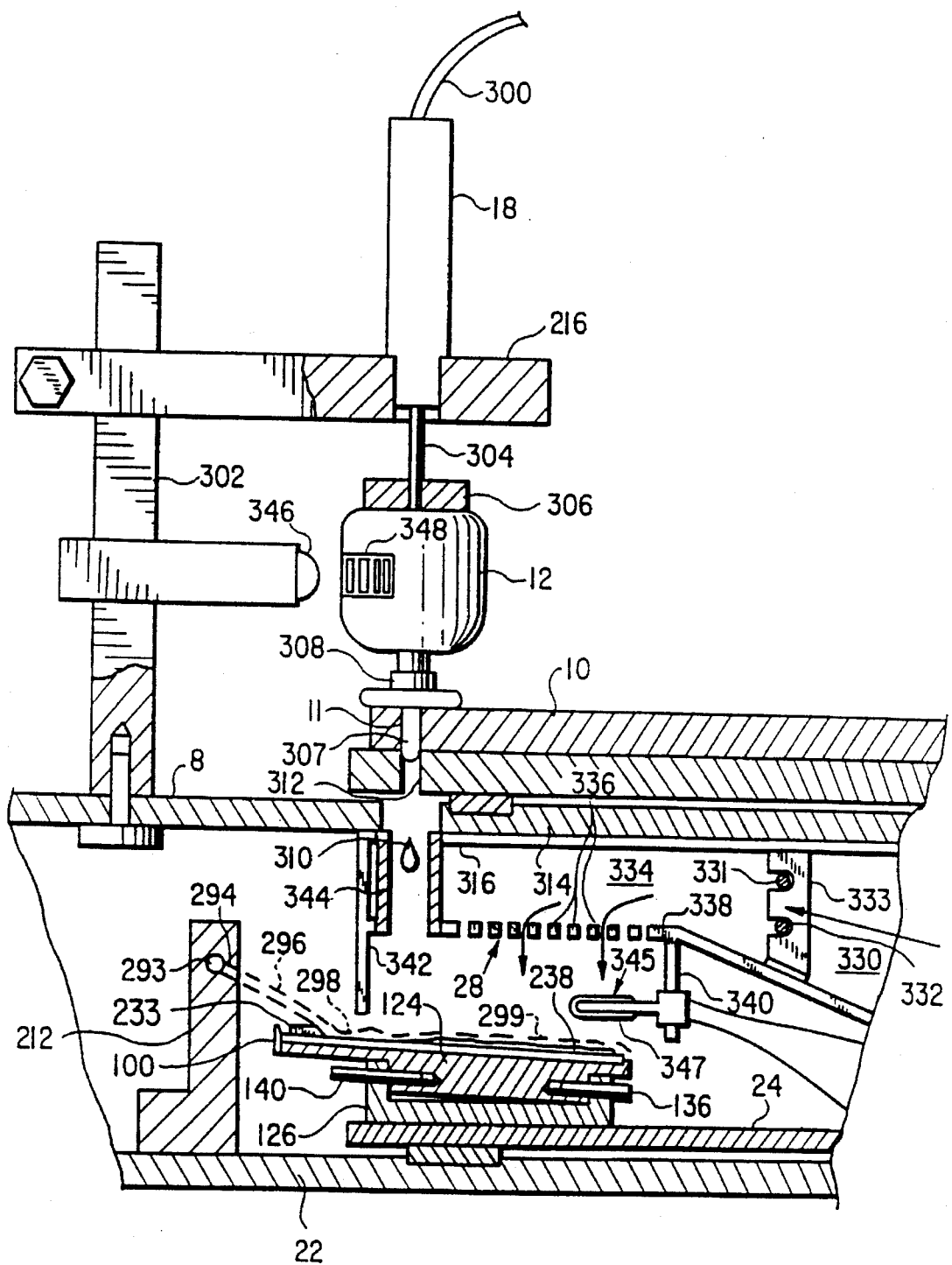
FIG. 15 is a schematic, fragmentary cross-sectional view of the evaporation inhibiting liquid and reagent receiving station, taken along the line B—B in FIG. 11.

Temperature controller 66, mounted on support plate 22, controls the heat energy supplied to the heated water container 44. Temperature controllers 68 and 70, mounted on support plate 40 (FIG. 4), control the temperature of the air in the heated air supply chamber 28 by controlling energy supplied to respective annular heater elements 331 and 332 (FIG. 15). Slide carousel stepper motor driver 72 and relay 74 operate stepper motor 48. Power supplies 76 and 78 provide power to the stepper motors and control systems. Air compressor 80 supplies air to the air filter 82 and air pressure regulators 38, 64 and 86.

Figure 5:
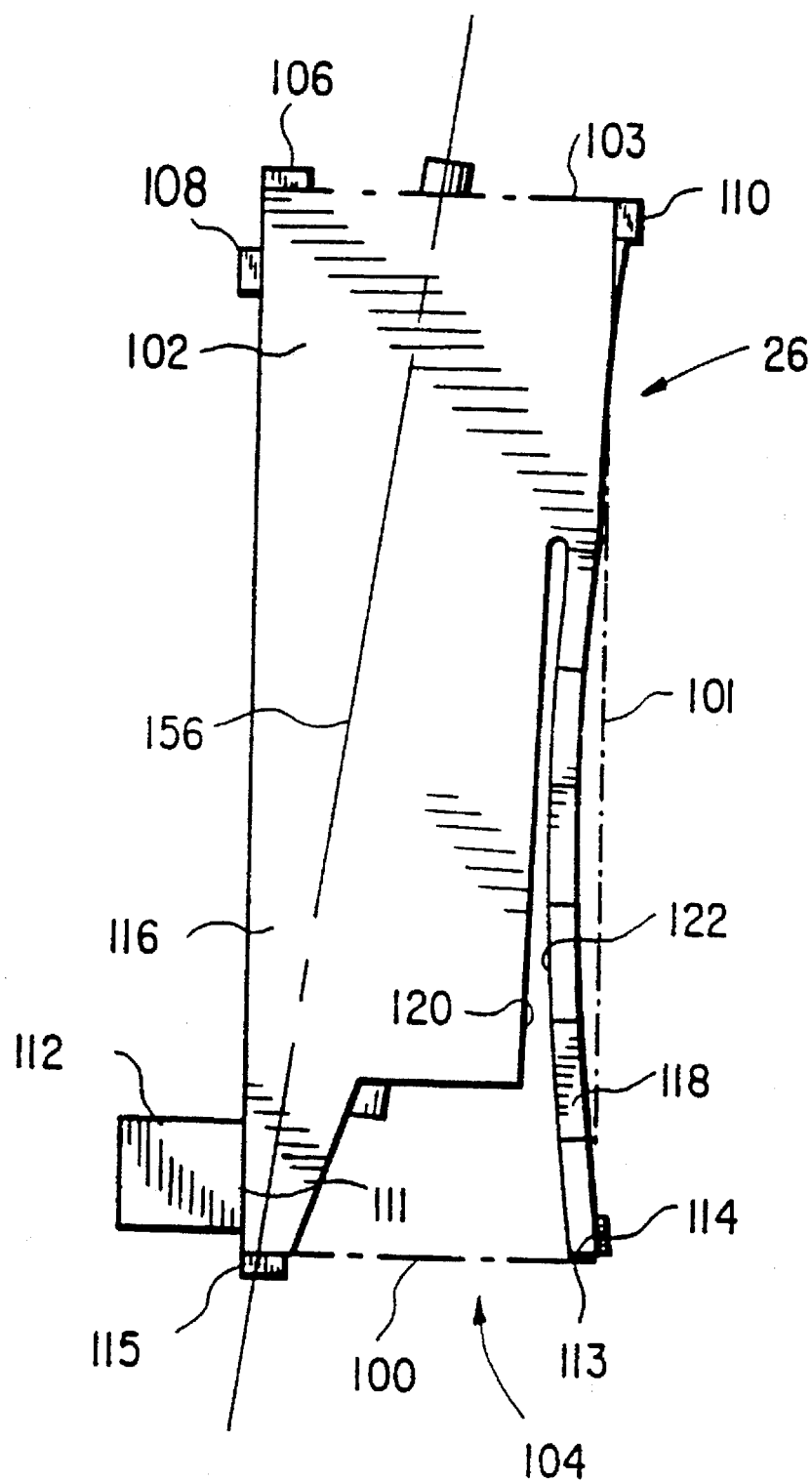
FIG. 5 is a top view of a pivotally mounted slide support.

FIG. 5 is a top view of a first embodiment of a mounted slide support 26 with slide edges 100 and 101 represented by dashed lines. The slide support 26 has a support plate 102 with a distal end 103 and a proximal end 104. The distal end 103 has a raised terminal guide end tab 106 and two lateral guide tabs 108 and 110 with the upper edges constituting guide tab termini. The distance between the upper surface of the slide support 26 and the guide tab termini (the elevation above the upper surface) is less then the thickness of a conventional microscope slide. The proximal end 104 of the slide support 26 has opposed lateral guides 112 and 114 for engaging the lateral edges of a slide and a terminal end tab 115 for engaging the proximal end of a slide. The proximal end 104 of the slide support 26 has an inflexible support portion 116 providing a lateral edge 120 and a flexible arm 118 including a lateral edge 122 positioned such that lateral edges 120 and 122 oppose one another. The distance between the slide edge engaging surfaces 111 and 113 of the guide tabs 112 and 114 is less than the width of a slide to be supported on the slide support 26. A standard slide has a width of 1 inch or 25 mm, and the preferred distance between the slide edge engaging surfaces 111, 113 of the tabs 112, 114 for supporting a standard slide is from 20 to 24 mm. The flexure of arm 118 permits positioning of the slide between the lateral guide tabs and terminal end tabs 106, 115. The distance between the opposing tab surfaces 111 and 113 causes the slide support 26 to apply a positive pressure on the edges of a slide, retaining the slide securely on the slide support 26 during the tilting and other processing steps. The upper surface of the support plate 102 is preferably planar and smooth so the wet slide rests closely on the surface 102, and surface tension will resist vertical movement of the slide from the support surface 102.

Figure 6:
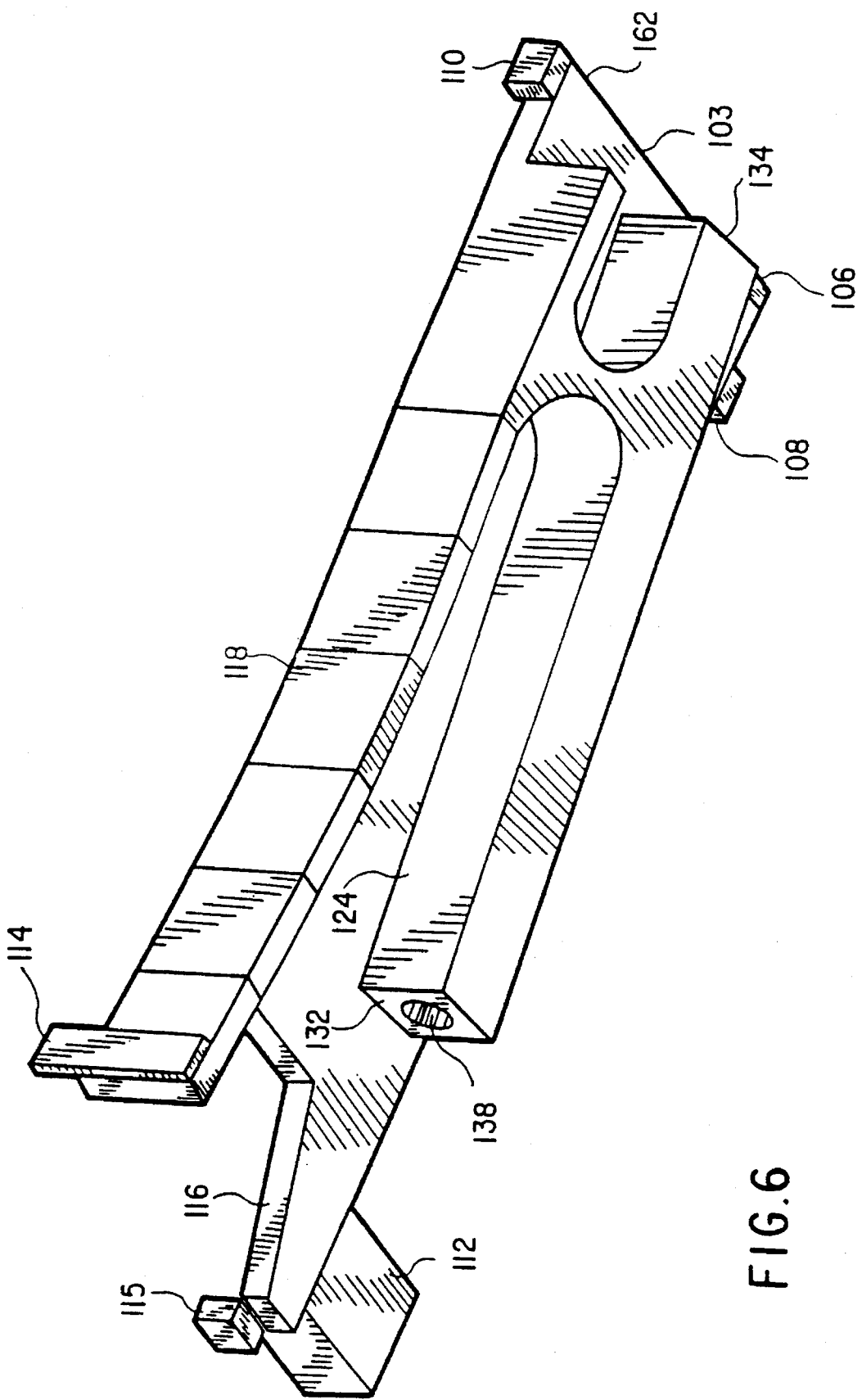
FIG. 6 is an isometric view of the underside of the slide support component.

FIG. 6 is an isometric view of the underside of the slide support 26. The inflexible portion 116 has an integral pivot support 124 which reinforces the inflexible portion 116 to prevent flexure. The flexible arm 118 has sufficient depth or thickness to limit the flexural movement of the arm 118 to a horizontal direction. This insures effective cooperation and pressure between the guide tab 112 on the inflexible portion 116 and the guide tab 114 on the flexible arm 118 to assist in retaining the slide in place on the slide support 26 during the tipping operation described in detail hereinafter.

Figure 7:
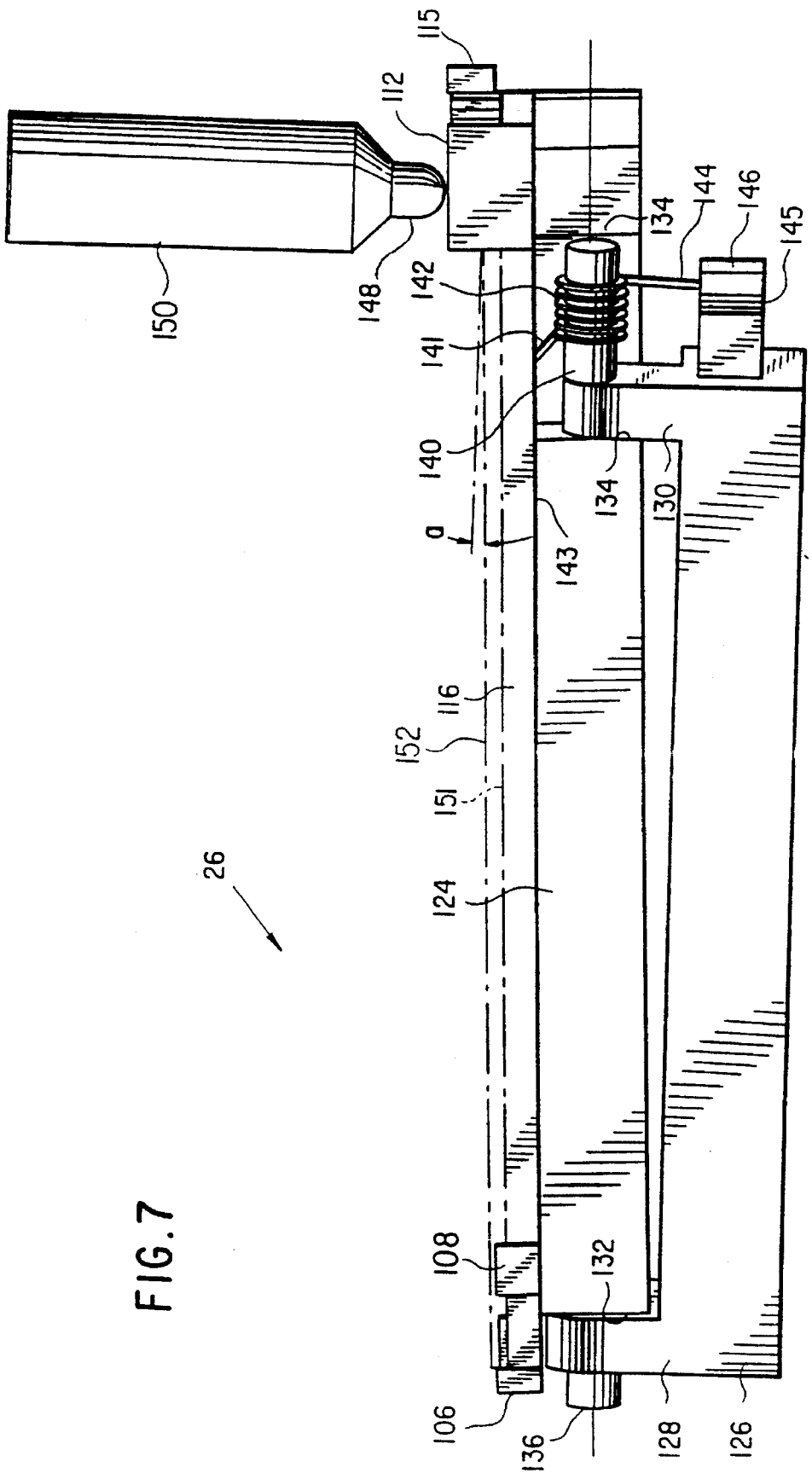
FIG. 7 is a side view of the pivotally mounted slide support of FIG. 5 showing the tipper and mounting details.

FIG. 7 is a side view of a mounted slide support showing the tipper and mounting details. The upper pivot support 124 is pivotally mounted on the lower pivot support 126. Lower pivot support 126 has upward extending projections 128 and 130 which engage the ends 132 and 134 of the upper pivot support 124. Pivot pin 136 extends through an axially aligned hole in projection 128 into an axially aligned receptor hole 138 (FIG. 6) in the opposing end 132 of the upper pivot support 124. At the opposite end, axially concentric with pivot pin 136, pivot pin 140 extends through a hole in projection 128 (not shown) into a respective receptor hole in the opposing end 134 of the upper pivot support 124. The slide support 102 is thus mounted for pivotal motion around the common pivot axis of the pins 136 and 140. Bias spring 142 is supported on pin 136, one end 141 pressing against the lower abutment surface 143 of the inflexible support portion 116, and the other end 144 bearing against spring stop groove 145 in the spring stop 146. The tip 148 of tipper 150 is positioned above the upper surface of guide tab 112 when the slides are positioned in a rinse station, described in greater detail hereinafter with respect to FIG. 13.

The pivot pins 136 and 140 support the upper surface of the slide support 102 at a small angle 'a' from the horizontal plane to aid liquid flow toward the distal end 103 during treatment. Angle 'a' is preferably in the range of from 0.3° to 1.0°. The upper surface 151 of the inflexible support portion 116 and the upper slide surface 152 (dotted line) supported thereon are thus maintained at a slight incline from the horizontal plane downward toward the distal end 103 of the slide support 26.

Figure 8:
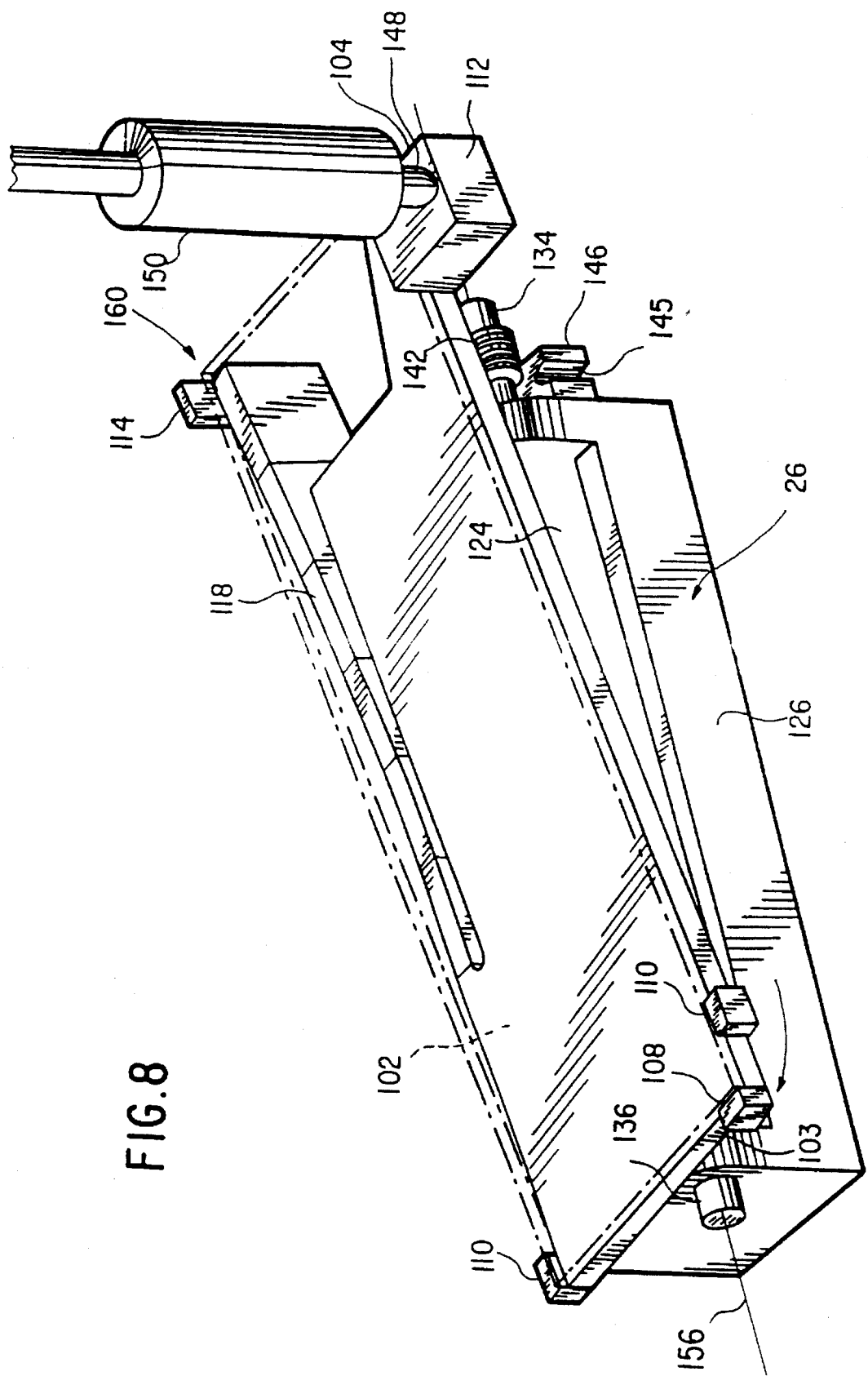
FIG. 8 is an isometric view of the mounted slide support of FIG. 7 in the untipped position.
Figure 9:
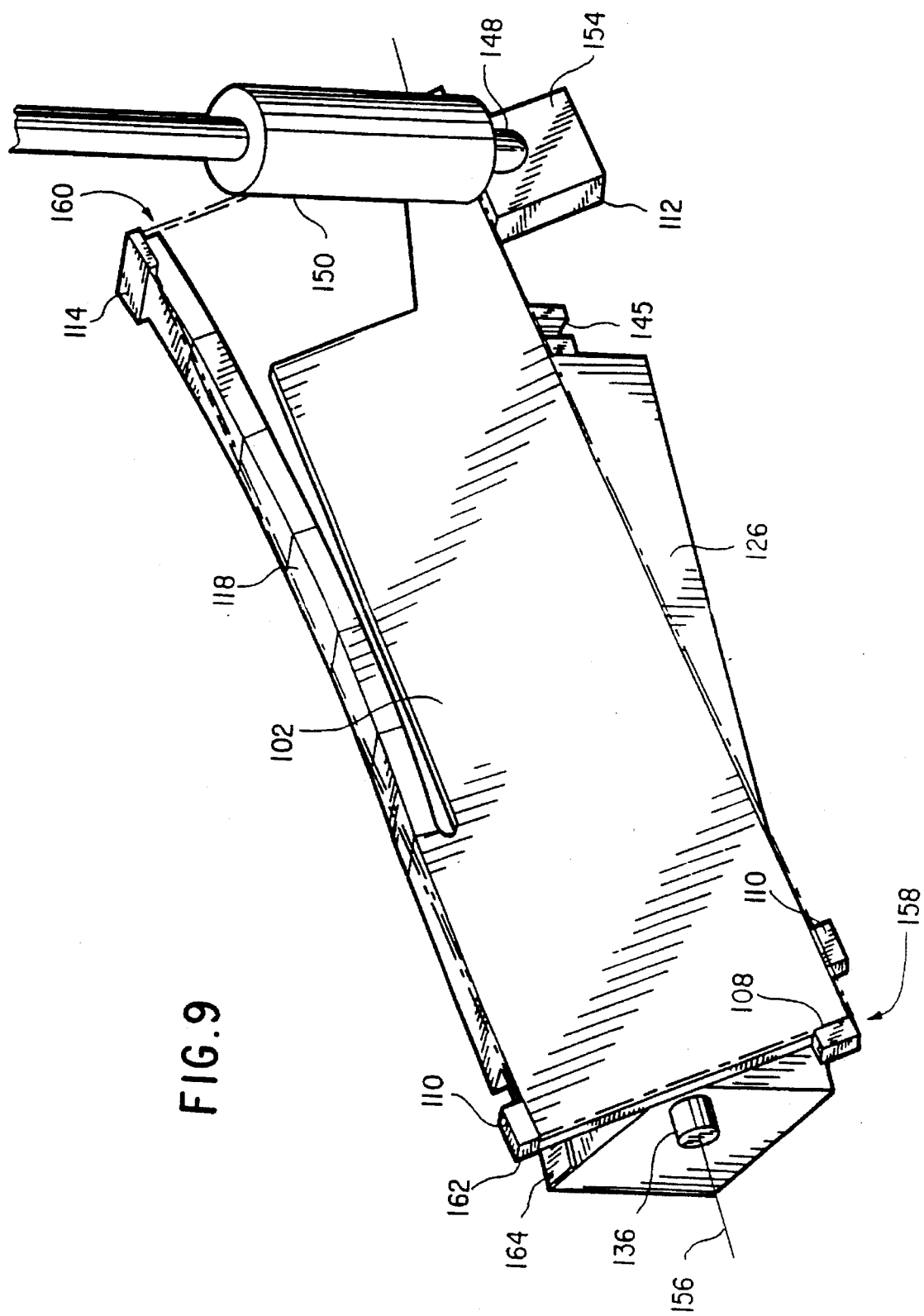
FIG. 9 is an isometric view of the mounted slide support of FIG. 7 in the tipped position.
Figure 10:
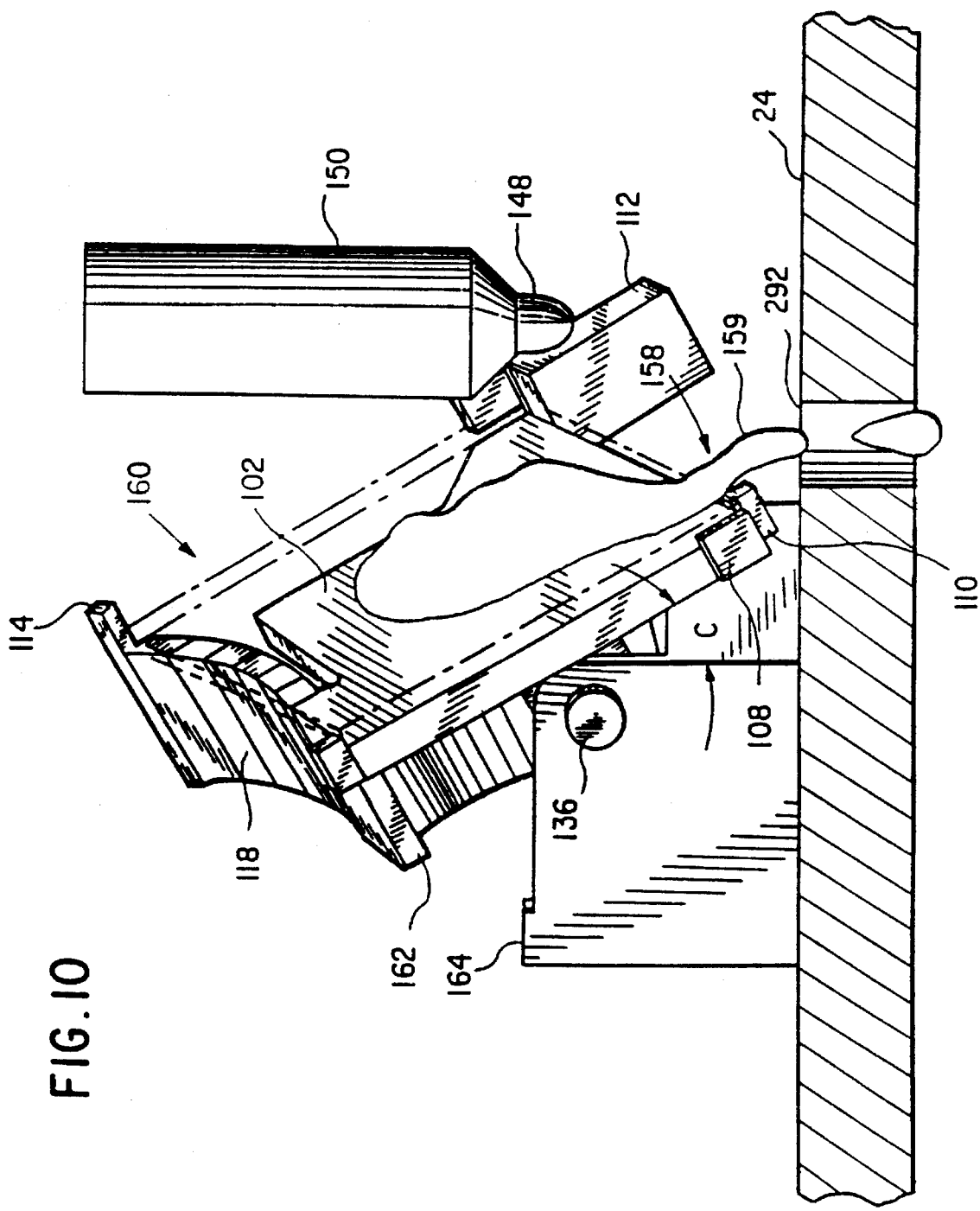
FIG. 10 is a distal end view of the mounted slide support in the tipped position.

FIG. 8 is an isometric view of a slide (dashed lines) mounted on slide support 26 in the untipped position, Fig. 9 is an isometric view of the mounted slide support 26 in the tipped position, and FIG. 10 is a distal end view of the mounted slide support 26 in the tipped position. Vertically downward pressure of the tipper tip 148 against the upper guide tab surface 154 of guide tab 112 rotates the support plate 102 about the pivot axis 156 defined by the pivot pins 136 and 140. The pivot axis 156 (FIG. 5) preferably lies in a vertical plane through the midpoint of distal end 103 and the left edge proximal end 104 of the slide support 26. The tipping action tilts the slide surface to an angle 'c' of approximately 60° from the vertical (FIG. 10). It sharply lowers distal corner 158 and sharply raises proximal corner 160, breaking the liquid meniscus on the slide surface and directing the liquid flow 159 to the corner 158 and off the surface of the slide into drain hole 292. The pivotal movement increases the pressure of the spring 142 against spring stop groove 145, and as the tipper 150 is raised, the slide support 26 returns to its original position. The slide support return pivot motion is terminated when distal corner 162 of the support plate 102 abuts stop surface 164 of the lower pivot support 126.

Figure 11:
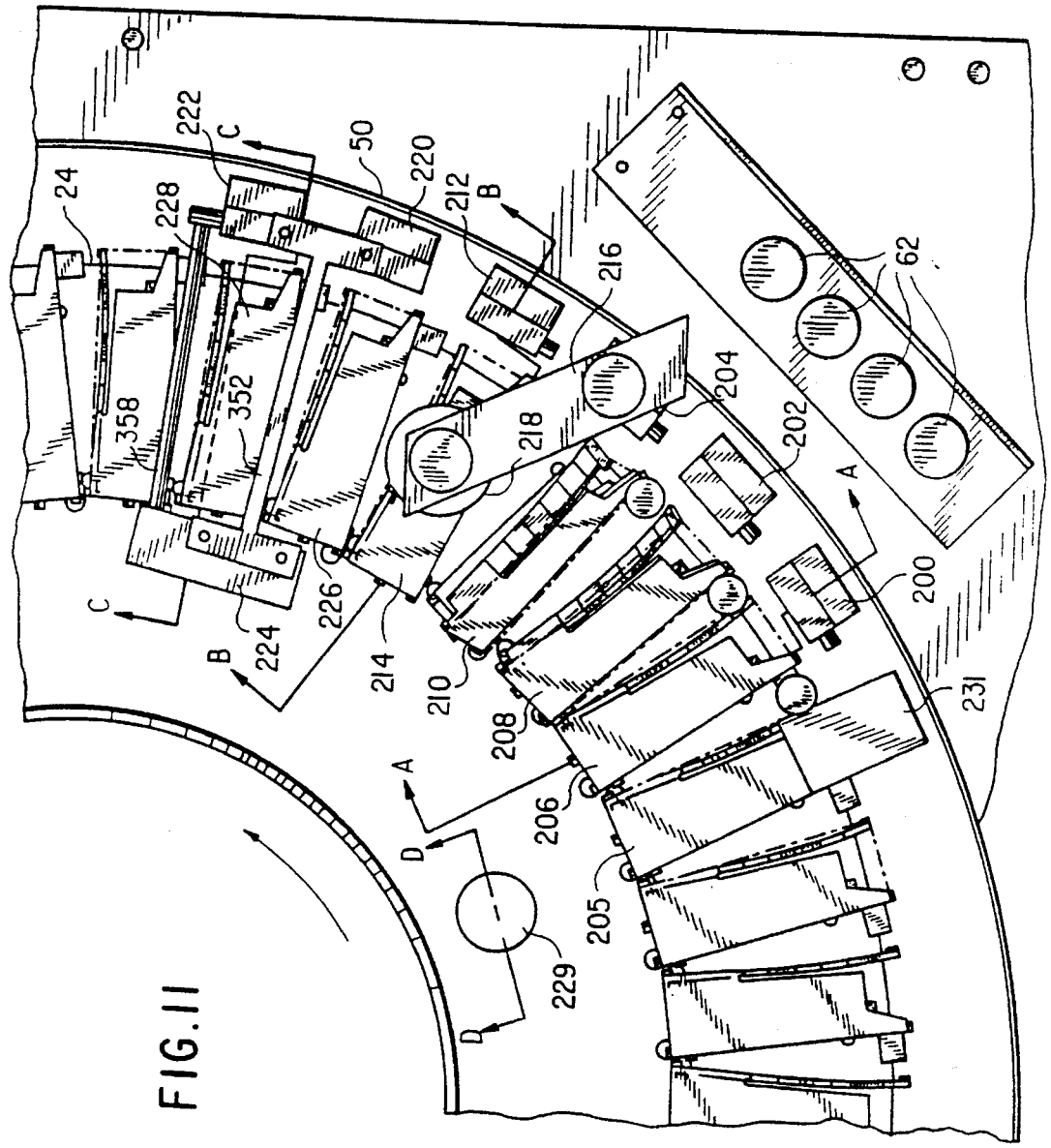
FIG. 11 a fragmentary top view of the slide support carousel showing details of the slide treatment stations.
Figure 12:
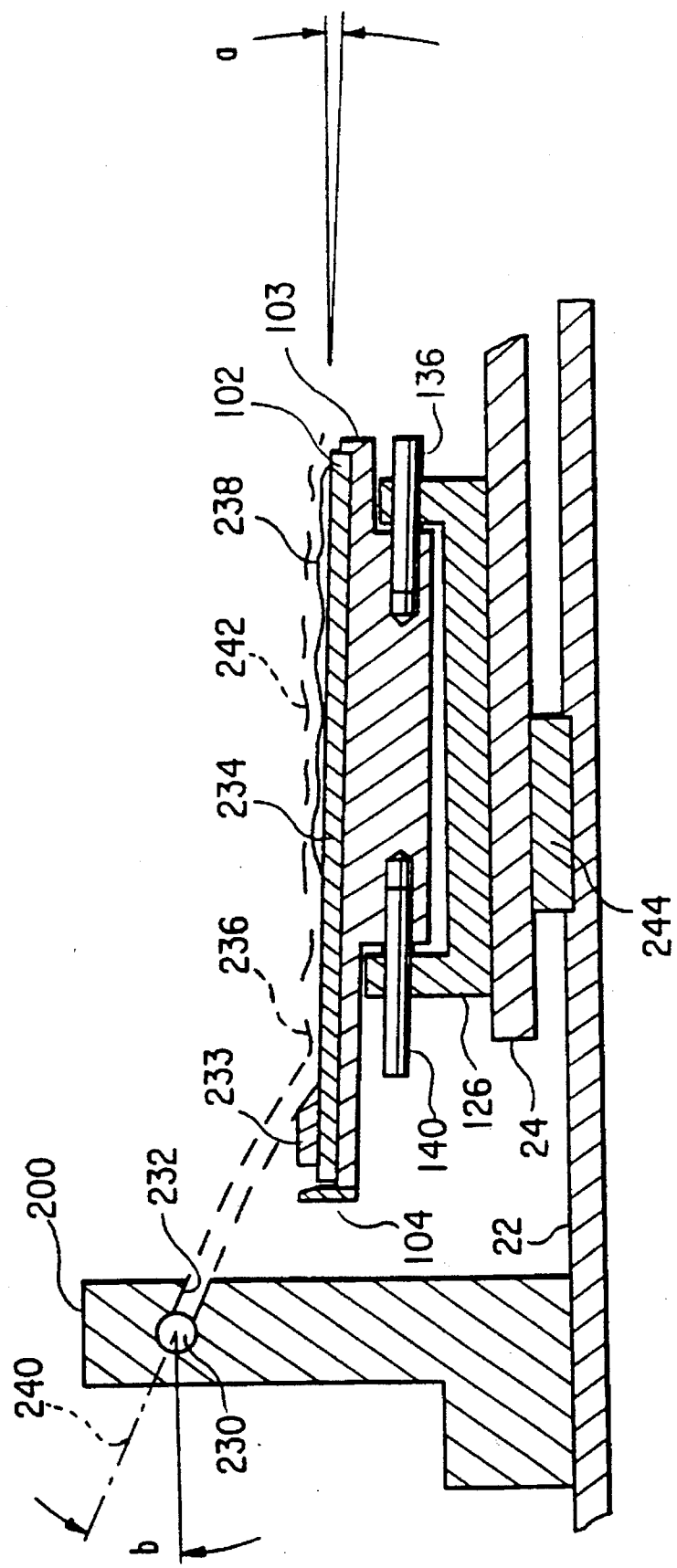
FIG. 12 is a schematic cross-sectional view of a rinse station taken along the line A—A in FIG. 11, showing details of rinse liquid flow on a slide.
Figure 13:
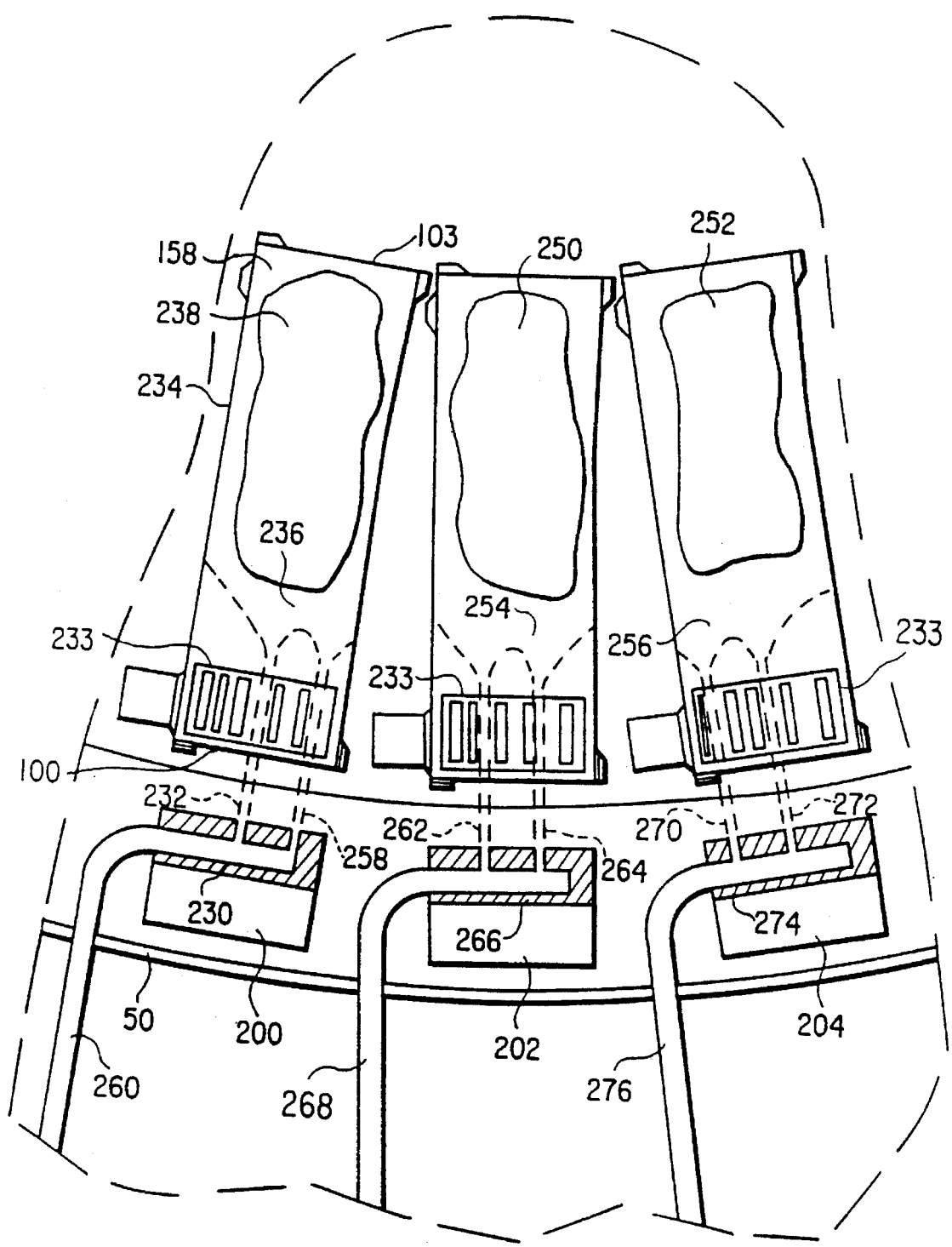
FIG. 13 is a top schematic view of the rinse stations showing details of the rinse liquid distribution on slides being treated therein.
Figure 14:
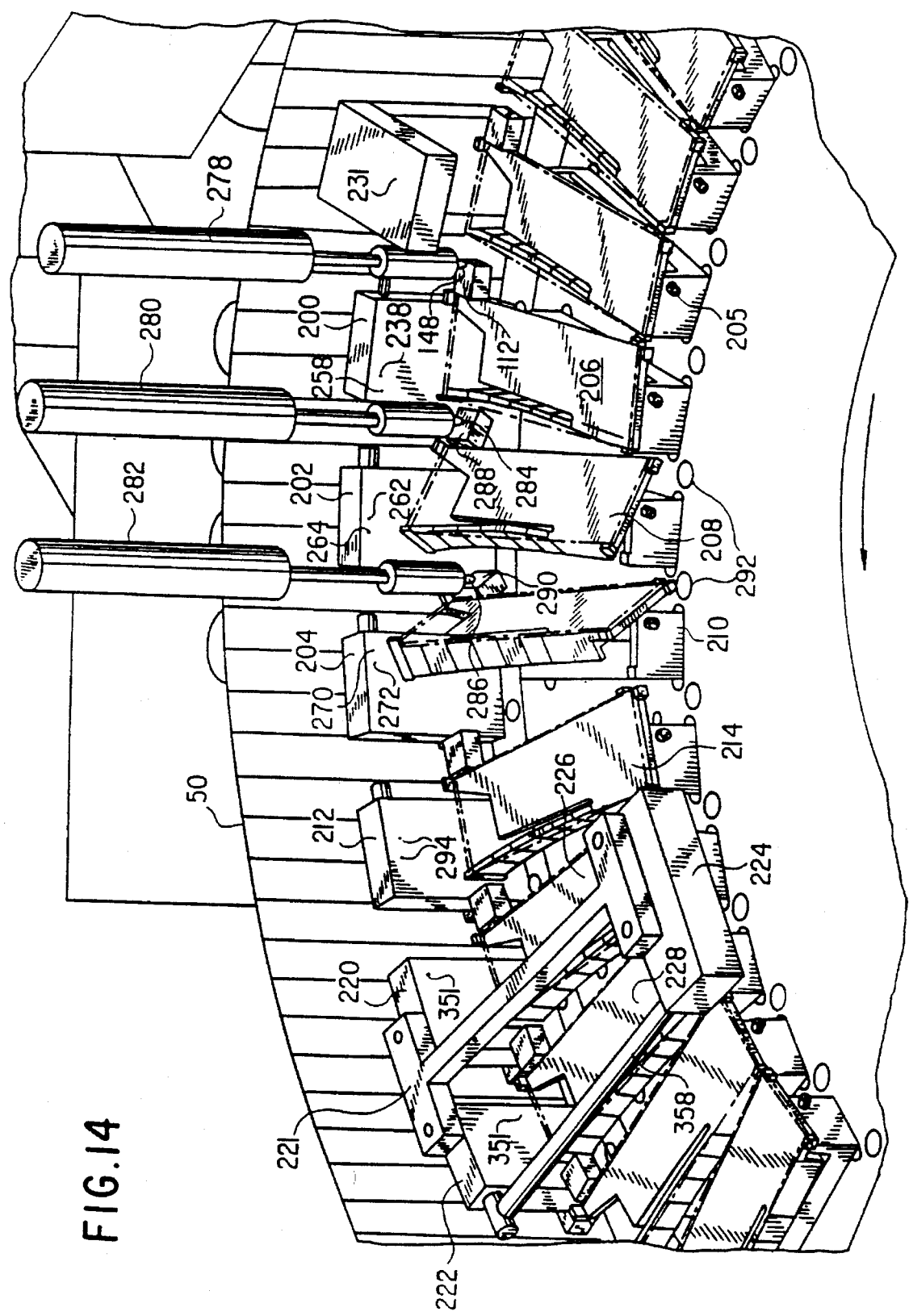
FIG. 14 is an isometric view of the slide treatment bar code reading, rinse, reagent receiving and vortex mixing stations.
Figure 16:
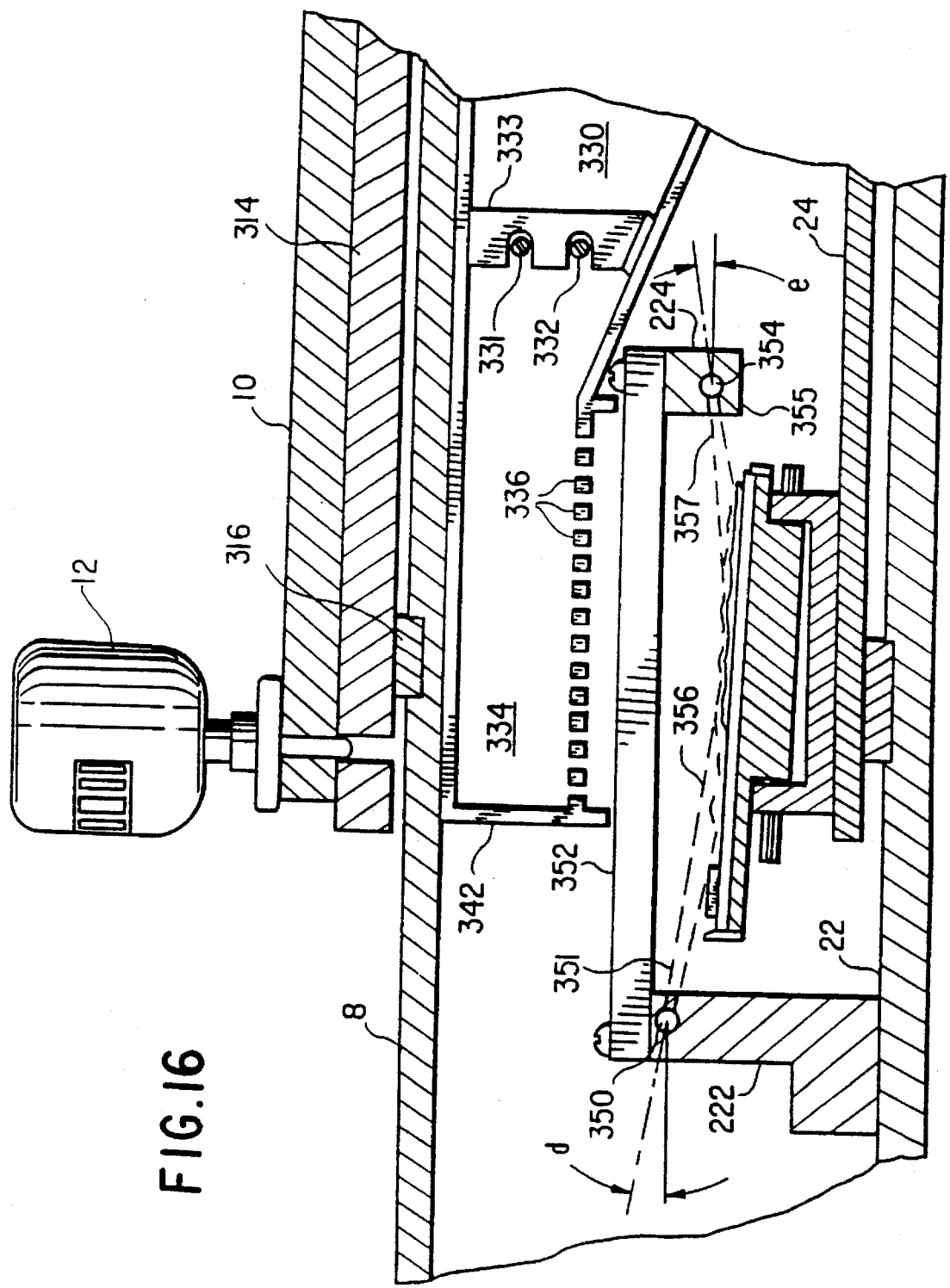
FIG. 16 is a cross-sectional view of the vortex mixing assembly, taken along the line C—C in FIG. 11.
Figure 17:
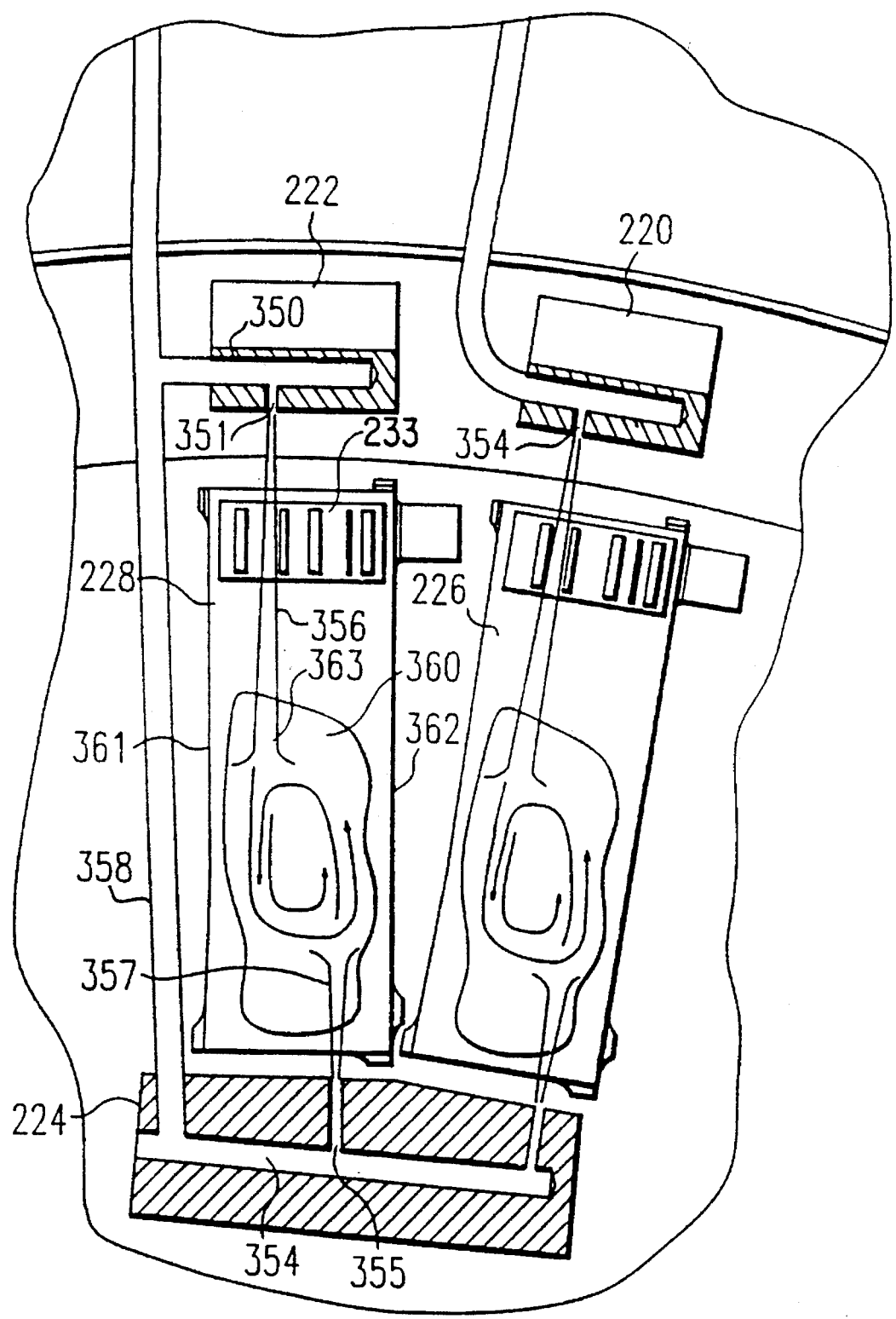
FIG. 17 is a top schematic view of the vortex mixing zone, showing details of the vortex mixing action.

FIG. 11 a fragmentary top view of the slide support carousel 24 showing details of the various slide treatment stations. Rinse nozzle blocks 200, 202 and 204 and the adjacent respective slides 206, 208 and 210 define successive rinse zones, details of which are shown in FIGS. 12–14. Evaporation inhibitor liquid application block 212 and the adjacent slide 214 define the evaporation inhibitor and reagent application zone, details of which are shown in FIG. 15. Air cylinder reagent delivery actuator 18, supported by support arm 216, contacts reagent bottle 218, directly over slide 214. Vortex mixer air jet blocks 220, 222 and 224 are positioned adjacent slides 226 and 228 in the agitation zone, details of which are shown in FIG. 16 and 17. The hanger 352 is mounted on the tip of blocks 220 and 222 and supports suspended block 224. Pressurized air is delivered to block 224 by conduit 358. As the slide support carousel 24 positions each slide for successive treatment in the rinse zones, evaporation inhibitor and reagent application zone, and agitation zones (counterclockwise movement of the carousel), the tissue sections on each slide are first rinsed and then covered with evaporation inhibitor. Reagent is applied from a preselected reagent bottle to the tissue through the evaporation inhibitor layer, and the reagent is agitated through the evaporator inhibitor layer by the vortex mixer. Each slide then is moved around the incubation zone, a circular path traveled by the slide support carousel 24, heated with hot air from the heated air manifold 30, and the reagent reacts with the sample. As the carousel 24 continues to increment around the circle, each slide is returned to the rinse stations, etc, for application of the next reagent required in the reaction. This entirely automated process continues until the desired reactions are completed.

Bar code reader 231 (FIG. 14) above slide 205 reads a slide bar code 233 (FIGS. 13 and 17) on each slide. The slide bar codes 233 identifies the slide sample and the particular immunohistochemical process required for that sample. This information is fed into the computer and correlated with the indexed position of that slide with respect to "home", to control the sequence of reagent chemicals to be applied to that slide in the reagent application zone.

FIG. 12 is a schematic cross-sectional view of a rinse station taken along the line A—A in FIG. 11, showing details of rinse liquid flow on a slide. Rinse block 200 mounted on plate 22 has a heated rinse liquid supply channel 230 communicating with rinse liquid nozzle 232. The slide 234 has a sloping surface at an angle 'a' being supported on the sloping surface of the slide support 102. The slide 234 has a rinse liquid impact zone 236 adjacent the proximal end 104 between the bar code 233 and the sample 238. The impact zone 236 is at a higher elevation than the tissue section 238 supported adjacent the distal end 103. The nozzle axis 240 has an angle 'b' which directs liquid against the slide surface impact zone 236. The impact zone 236 is above the tissue section 238 on the sloped surface of slide 240, and the rinse liquid stream 242 flows across the upper surface of the tissue section 238 toward the distal end 103. The angle 'b' preferably has an angle of from 15° to 35°, and the distance between the exit of nozzle 232 and the slide 124 is selected to direct the rinse liquid precisely on the impact zone 236, avoiding disturbance of the fragile tissue section 238.

The slide support carousel 24 is rotated above the plate 22, the outer periphery being supported by low friction slide bearings 244 arrayed in an axially concentric circular path on plate 22 under the outer periphery of carousel 24.

FIG. 13 is a top schematic view of one embodiment of the rinse stations showing details of the rinse liquid distribution on slides being rinsed therein. Slides 234, 246, and 248 are positioned in the path of heated rinse solutions (dotted lines) from rinse station blocks 200, 202 and 204. Fragile tissue sections 238, 250 and 252 are positioned adjacent the distal end of the slides. The rinse liquid impact zones 236, 254 and 256 are positioned between the tissue sections and the proximal ends of the slides, to avoid direct impact of the liquid jets from the rinse block nozzles. The rinse nozzles on each block are preferably 11.5 mm apart. Rinse block 200 has right offset nozzles 232 and 258 (offset 2 mm to the right of center) supplied by channel 230 connected to supply tubing 260. This directs the rinse fluid toward the right surface of the slide, effecting a transverse flow path across the tissue section 238 to the distal end drain corner 158. Rinse block 202 has symmetrical nozzles 262 and 264 supplied by channel 266 connected to supply tubing 268. The symmetrical nozzle configuration effects a central flow path across the tissue section 250. Rinse block 204 has left offset nozzles 270 and 272 (offset 2 mm to the left of center) supplied by channel 274 connected to supply tubing 276. The left offset nozzles 270 and 272 direct a rinse flow path down the left side of the tissue section 252. The nozzle patterns provide effective rinse solution flow distribution across all portions of the tissue section surface as the slide is treated in each successive rinse section.

FIG. 14 is an isometric view of the rinse stations, a evaporation inhibiting liquid and reagent application station, and agitation stations, showing details of the slide tipping action in the rinse sections. Tipper air cylinders 46 (FIG. 3 and 4) comprises three conventional air cylinders 278, 280 and 282 with internal pressurized air activated pistons or equivalent actuators. Pressurized air delivery to the cylinders causes respective tipper tips 148, 284 and 286 to move downward, pressing against respective slide support tabs 112, 288 and 290. Three tipper positions are shown to illustrate the action thereof. Tipper tip 148 is shown in the fully withdrawn or resting position, and slide 206 is in the rinse solution receiving position. After application of heated rinse solution, the tipper descends through an intermediate position shown by tipper tip 284 and slide support 208, to the drain position shown by tipper tip 286 and slide support 210. Liquid drains from the left distal corner (lowest corner) into a drain hole 292.

In each rinse station, the sample is treated with a repeated, preferably at least seven, rinse cycles. Each rinse cycle comprises application of approximately 500 µL of heated rinse solution in a short pulse (120 msec) to the slide, followed by tipping the slide to drain away the rinse solution. An estimated 150 µL of liquid remains on the slide after draining. These rinse cycles are repeated in each rinse station. The short rinse pulse followed by draining prevents the formation of a equilibrium solute boundary layer and greatly increases the rinse efficiency, overcoming the boundary problems present in the prior art rinse methods. Assuming that 150 μL of rinse solution is left after each draining step, a 23 percent dilution is achieved with each rinse cycle. Thus the effective dilution in the combination of the three rinse stations is estimated to be 0.2 parts per trillion, many orders of magnitude more effective than prior art, biochemical rinse procedures. This greatly increases the sensitivity of the immunohistological process.

FIG. 15 is a schematic, fragmentary cross-sectional view of the evaporation inhibiting liquid and reagent application station, taken along the line B—B in FIG. 11. Evaporation inhibitor liquid distributor block 212 has a supply channel 293 and outlet nozzles 294.

The evaporation inhibiting liquid is substantially water-insoluble, substantially water-immiscible and substantially thin or non-viscous. It has a specific gravity less than water, and a boiling point above the process temperature, preferably above 100° C. It should be devoid of chemical characteristics which would significantly interfere with biochemical reactions carried out on the sample, that is, the reactions taking place between the reagents and tissue sample on the slide. Preferred evaporation inhibiting liquids are hydrocarbons, optimally non-aromatic saturated hydrocarbons, having from 9 to 18 carbons, most optimally having about 10 to 14 carbon atoms.

A small quantity of evaporation inhibitor liquid is directed by nozzle 294 in a inhibitor liquid stream 296 to an impact zone 298 on the slide between the tissue sample 238 and the proximal end 100 of the slide, so that the tissue sample is not disturbed. The evaporation inhibitor liquid flows across the surface of the water layer on the wetted tissue, forming a thin evaporation inhibiting film 299 over the aqueous layer which usually covers most of the upper surface of the slide. The tissue is now ready for application of reagent.

The reagent delivery combination includes a conventional air cylinder 18 or equivalent actuator having an internal pressurized air activated piston. It is supplied with pressurized air by tubing 300. Air cylinder 18 is supported by plate 216 and post 302 mounted on upper plate 8. Delivery of pressurized air to the cylinder 18 causes rod 304 and its attached foot 306 to move downward against a reagent container 12 positioned in the reagent delivery zone. Downward movement of reagent container 12 causes emission of a precise volume of reagent liquid 310. Suitable volumetric pumps are available from S. A. Valois and are described in U.S. Pat. No. 4,245,967 and French patent 2,528,122.

The reagent carousel support 314 is the drive plate which supports the reagent bottle carousel 10 and rotates it about its axis to place a predetermined reagent bottle 12 in the reagent delivery zone. An axially concentric circular array of low friction slide bearings 316, mounted on the upper plate 8, are positioned under the outer edge of the reagent support carousel.

The predetermined volume of aqueous reagent 310 impacts the evaporation inhibitor surface film between the impact zone 298 and the upper edge of the tissue sample 299, passing through the film to the aqueous layer beneath the film and reaching the slide surface. The reagent then flows across the tissue sample 238 under the covering film of evaporation inhibiting liquid 299. In this sequence, immediately after leaving the rinse stations, the slide is covered with the protective film to prevent any dehydration of the tissue sample 299. The reagent solution is then applied to the protected tissue. Dehydration of the tissue section would irreversibly alter its physical and chemical characteristics and impair the immunohistochemical reactions. Dehydration is a constant hazard because of the constant flow of heated air over the slides required to maintain them at the desired temperature. The heated air temperature is determined by the requirements of the biochemical processes required by the process. It is slightly above 40° C., preferably about 45° C., for immunochemical reactions and can be as high as from 93° to 97° C. for in situ DNA hybridization reactions.

FIG. 15 also shows detailed elements of the heated air supply chamber 28 shown in FIG. 1. Air is moved upward into the central intake manifold chamber 330 and through annular heating coils 331 and 332 mounted on annular air passageway plate 333, to heat the air to a temperature slightly above 40° C., preferably about 45° C. A higher temperature can be provided as needed for in situ DNA hybridization procedures. The heated air passes through the outlet manifold chamber 334 and out the outlet passageways 336 in the lower plate 338. Annular, axially concentric inner and outer heated air flow control curtains 340 and 342 direct the heated air downward over the slide surface. The reagent 310 falls through manifold passageway 344 to the slide surface.

The air temperature is monitored by heat sensor 345 positioned in the path of the heated air. A preferred heat sensor is a thermistor encased in a heat sensitivity adjusting jacket 347 which reduces the sensitivity of the thermocouple and approximates the thermal mass of the slides.

A reagent bar code reader 346 can be mounted on post 302, positioned to scan a reagent bar code 348 on the reagent bottle 12. Bar code 348 identifies the contents of the reagent bottle. At the beginning of a slide treatment operation, the reagent carousel 10 is rotated past the bar code reader 346, and the bar code 348 on each reagent bottle 12 is scanned. The scanned information is fed to the computer and correlated with the indexed position of the reagent carousel 10. This information is used to rotate the reagent carousel 10 to place the correct reagent bottle 12 in the application zone for each slide treatment step for each slide.

FIG. 16 is a cross-sectional view of one embodiment of the vortex mixing assembly, taken along the line C—C in FIG. 11. Outer vortex jet block 222, mounted on plate 22, has an pressurized air supply channel 350 and nozzle 351. Nozzle hanger 352 is mounted on the top of vortex block 22 and supports suspended inner vortex air jet nozzle block 224. Channel 354 supplies nozzle 355 in block 224 with pressurized air. Nozzles 351 and 355 have central axes which form angles 'd' and 'e' of from 5° to 15° with the horizontal, directing air jets 356 and 357 toward the slide surface at the corresponding acute angles.

FIG. 17 is a top schematic view of the vortex mixing zone, showing details of the vortex mixing action. Pressurized air is supplied to the nozzle channels 350 and 354 by channel 358. The reagent solution covered by a layer 360 of evaporation inhibiting liquid 360 is stirred on the surface of the biological sample by applying at least one gas stream 356 or 357 to an area of the surface of the evaporation inhibiting liquid layer 360 between the center of the evaporation inhibiting layer 360 and the edge of the planar support surface 361 or 362 of the slide 228. The gas stream impacts the surface of the evaporation liquid surface layer 360 and moves the underlying reagent solution in a circular path on the tissue section. Preferably, the reagent solution is stirred on the surface of the biological sample by a vortex formed by applying two gas streams 356 and 357. Stream 356 is directed against a area 363 of the surface of the evaporation inhibiting liquid layer between the center of the evaporation inhibiting layer and the slide edge 361. Stream 357, in a direction opposite to the direction of stream 356, is directed against an area 364 of the surface of the evaporation inhibiting liquid layer between the center of the evaporation inhibiting layer and the slide edge 362. Although this method is shown with respect to an evaporation liquid inhibitor covered reagent layer, it will be readily evident that it can be applied to gently stir any liquid layer overlying a fragile substance.

FIG. 18 is a schematic representational cross-sectional view of a slide 370 following the rinse liquid, evaporation inhibitor and reagent application steps. Following the rinse stages (Stage A), the tissue section 371 mounted on slide 370 is covered with a thin residual aqueous layer 372. Following application of the evaporation inhibitor liquid (Stage B), the aqueous layer 372 and tissue section 371 is entirely covered by a layer 373 of the evaporation inhibitor liquid. Aqueous reagent 374, applied to the slide, flows under the evaporation inhibitor layer 373 to cover the tissue section. In the vortex mixing section (Stage C), air jets directed against the surface of the evaporation inhibitor liquid 373 move it and the reagent solution 374 thereunder in a swirling or stirring action on the surface of the fragile tissue section. This gentle stirring achieves increased interaction of reagent with the tissue section while preserving the tissue from dehydration or other damage from the air jets.

Figure 19A:
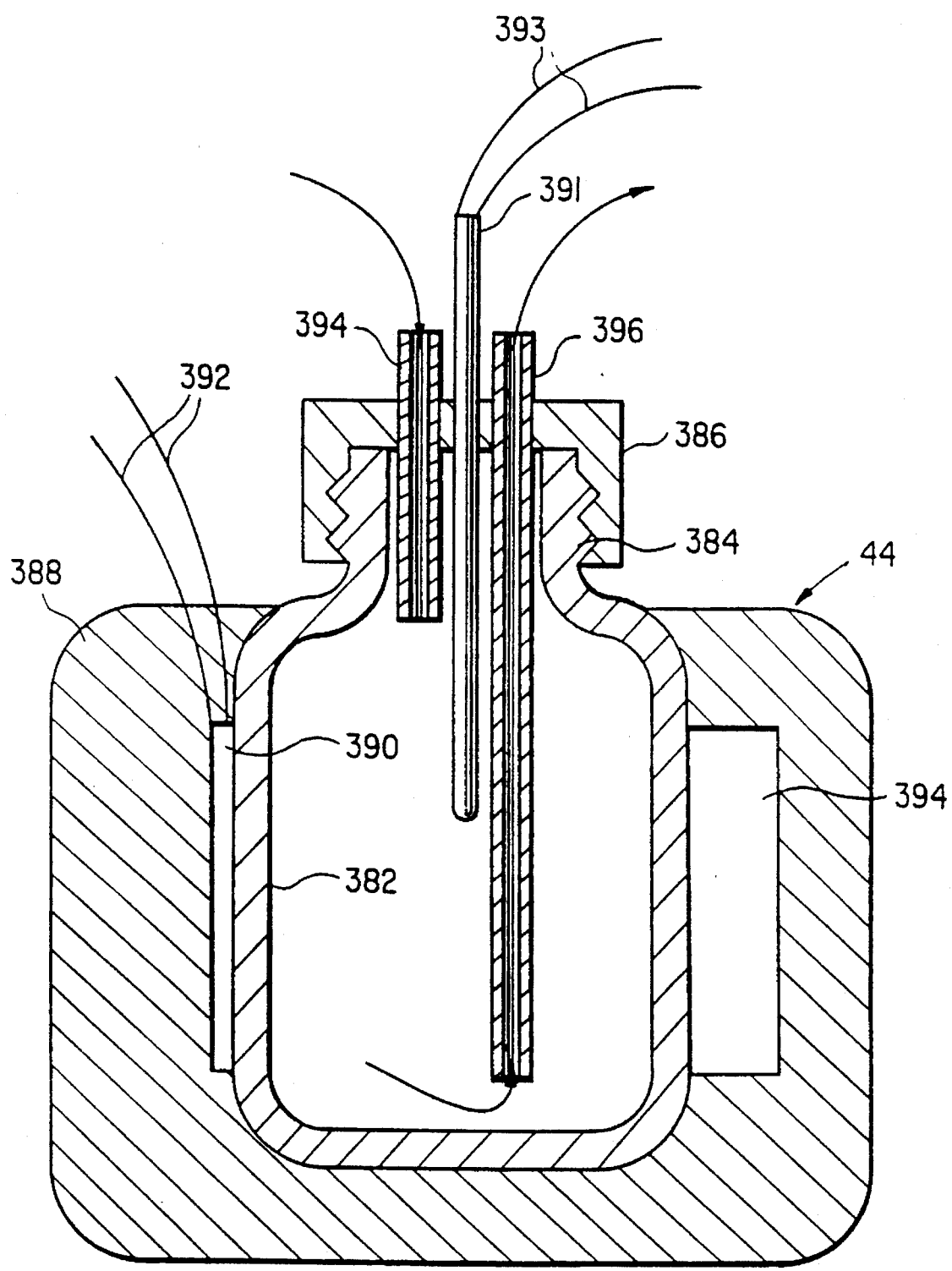
FIGS. 19A–19B are cross-sectional views of respective alternative embodiments of a rinse liquid container and associated heating components.

FIG. 19A is a cross-sectional view of one embodiment of a rinse liquid container and associated heating components. The rinse liquid applied to the surface of the slides by rinse blocks 200, 202 and 204 should have a temperature above 40° C. and is preferably about 45° C. The elevated temperature is critical for the immunochemical reactions. The rinse liquid is supplied by the hot water supply 44. The hot water supply 44 comprises an inner container of an inert material having a low coefficient of expansion such as a pyrex bottle 382 having a threaded neck 384 to which a cap 386 is attached by threads. The container 382 is surrounded by an insulating jacket 388 of suitable insulation material such as a fiberglass layer. Between the insulating jacket 388 and the bottle 382 is a heating jacket 390 with electrical power leads 392. A suitable heating jacket is a thick sheet of silastic rubber (polysiloxane) with embedded resistance heating coils having a combined heating value of about 180 watts. A conventional safety thermostat 394, connected to the elements of the heating jacket, is also provided between the insulating jacket 388 and bottle 382. The safety thermostat prevents the rinse liquid temperature from exceeding a preset value, preferably about 50° C. A thermistor temperature sensor 391 with leads 393 extends through the cap 386 into the upper zone of the bottle 382. An liquid inlet tube 394 extends through the cap 386 to the bottom of the neck 384, and an outlet tube 396 extends through the cap 386 to the bottom of the bottle 382.

This unique configuration provides a highly uniform liquid output temperature. The colder water entering through the inlet tube 394, being more dense than the heated liquid in the bottle, sinks downward past the heated container walls and is heated. The displaced liquid rises upward in the container. This stirring motion thoroughly mixes the liquid without the need for an agitator, producing a highly uniform outlet liquid temperature. Thermistor 391 constantly monitors the liquid temperature, providing a signal to the control system which is used to determine when the heating elements in jacket 390 should be energized.

Figure 19B:
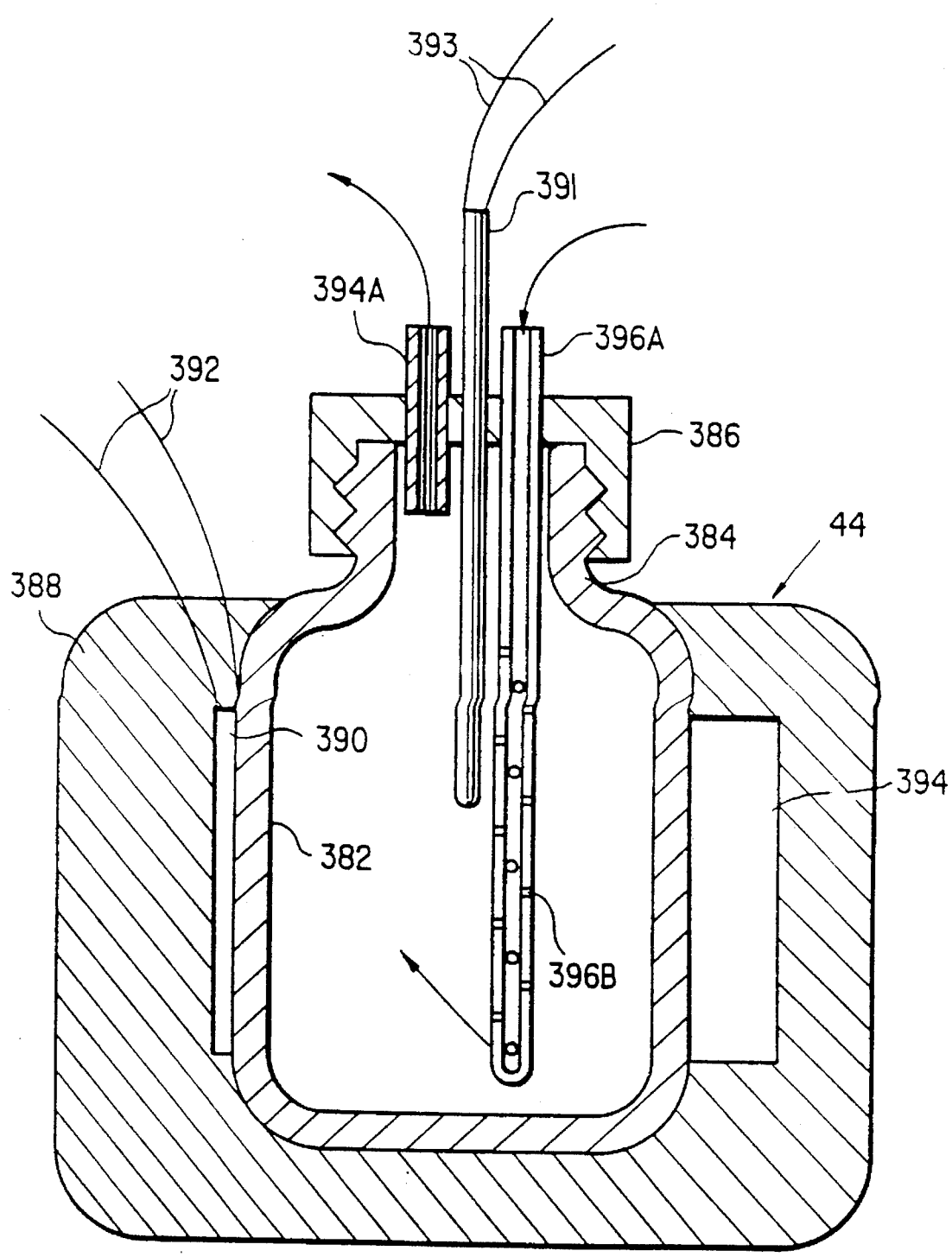

FIG. 19B illustrates an alternative embodiment of the rinse liquid container and associated heating components of the present invention which is similar to the structure illustrated by FIG. 19A except that the inlet tube 394 of the embodiment of FIG. 19 functions as an outlet tube 394A and outlet tube 396 of the embodiment of FIG. 19 functions as an inlet tube 396A, i.e., the inlet and outlet lines have been reversed. This arrangement prevents the build up of air or gas in the bottle 384. Additionally, the inlet tube 396A has been provided with perforations 396B for obtaining mixing as the bottle 384 is replenished with liquid.

Figure 20A:
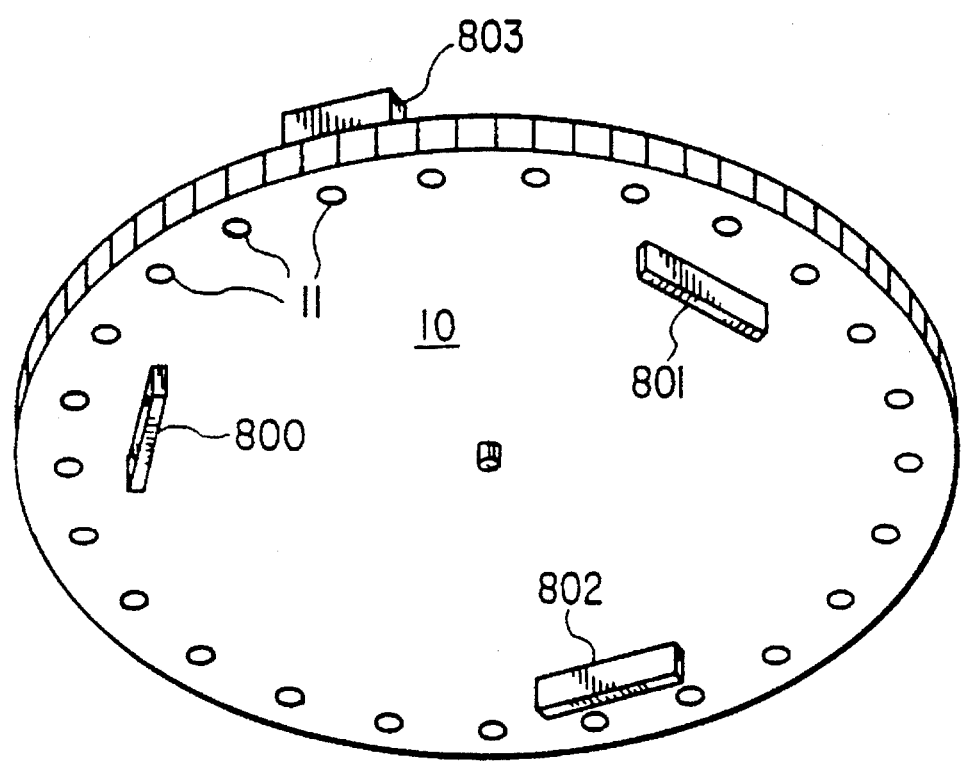
FIG. 20A is a bottom, isometric view of one embodiment of a reagent container support tray.

FIG. 20A is a bottom, isometric view of one embodiment of a reagent container support carousel 10. According to this embodiment, the reagent container carousel 10 has feet 800, 801 and 802 which rest in respective matching recesses in the reagent carousel support 314 (FIG. 15) in only one position. This insures that the reagent carousel 10A and the reagent bottle receptors 11 are always positioned in predetermined orientation on the carousel support 314.

The feet 800, 801 and 802 also function as supporting feet when the reagent support carousel 10 is removed. Refrigeration of the reagents is often required during their storage. The reagent container carousel 10, with the reagent bottles supported thereon, can be lifted from the carousel support 314 and placed in a refrigerator, supported by the feet 800, 801 and 802.

Indexing metal homing block 803 is mounted on the reagent container carousel 10 and rotates with the carousel 10. A conventional metal proximity detector (not shown) is mounted on the upper plate 8 at an position which places it adjacent the rotational path of the homing block. A change in electrical signal from the proximity detector indicates that the metal homing block is in the 'home' position adjacent the block.

FIG. 20B is an alternative embodiment of a reagent support carousel 10A and associated carousel support 314A wherein a handle 804 has been provided to assist in the removal and replacement of the reagent support carousel 10A as described above. In this embodiment, the carousel 10A is provided with a plurality of feet 800A, for example, five feet, which are substantially cylindrical elements with beveled edges 805, and fit into corresponding and matching circular openings 802A, formed in the associated carousel support 314A. The feet 800A and opening 802A are positioned so that the carousel 10A will fit into the support 314A in only one position such that the carousel 10A is always positioned in a predetermined orientation on the support 314A. The support 314A is provided with a central hub 806 which is received in a central opening 807 formed in the carousel 10A, the hub being provided with beveled edges 808. Engagement of the carousel 10A and the support 314A is best seen in FIG. 20C. Except for the above described differences, the carousel 10A and the support 314A are the same as previously described.

FIG. 21 is a fragmentary cross-sectional view taken along the line D—D in FIG. 11. Indexing block 229 is a metal block. Proximity sensor 610 is supported on the underside of plate 22 by bracket 611. The proximity sensor 610 emits an electrical signal through leads 612 which changes when the metal block 229 is positioned in the 'home' position immediately above the sensor.

The homing systems of the reagent carousel 10 and slide support carousel 24 operate in a similar manner. Presence of an indexing block adjacent the sensor produces a signal indicating that the carousel is in a "home" position, and provides a reference for subsequent indexed movements of the respective stepper motor drive and subsequent indexed movements of the respective carousel.

Figure 22:
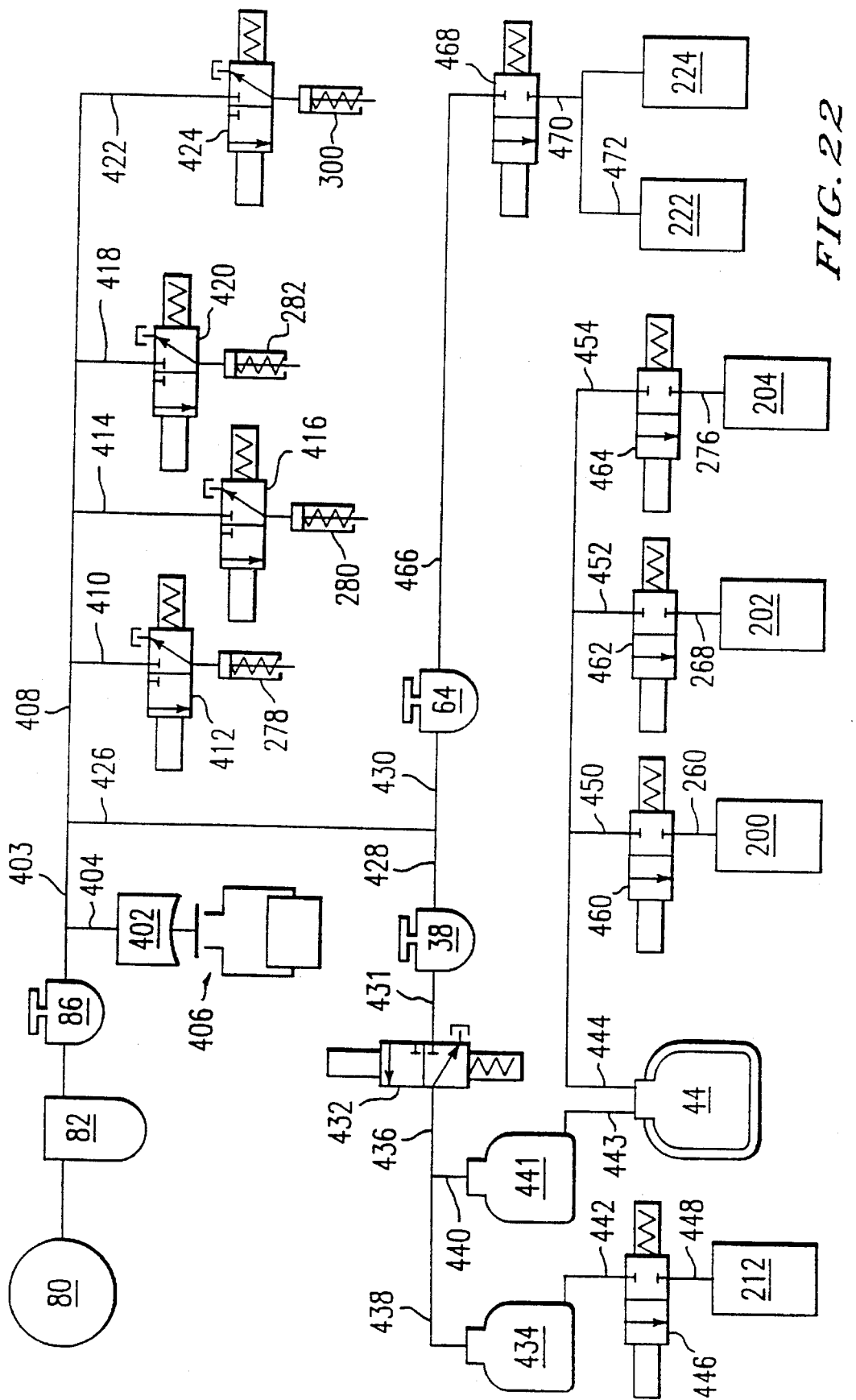
FIG. 22 is a schematic view of the pneumatic system of the automated immunostaining apparatus of this invention.

FIG. 22 is a schematic view of the pneumatic system of the automated immunostaining apparatus of this invention. The air supply for the system is supplied by air compressor 80 and air filter 82. The output line 400 from the air filter 82 is connected to the input port of air pressure regulator 86 where it is regulated to a constant output pressure of about 25 psi. Diaphragm pressure switch 402 communicates with the air pressure regulator 86 outlet line 403 through line 404. Diaphragm pressure switch 402 closes the system circuit breaker 406 when the pressure in line 404 is at least 22 psi. Failure of the air compressor and resulting drop in line pressure automatically deactivates the system.

The air output branch line 408 lead is connected by line 410 with tipper air cylinder three way control solenoid valve 412. When in an "open" position, solenoid valve 412 provides communication between input line and cylinder 278. This permits pressurized air to pass from line 410 to air cylinder 278, thus pressing tipper tip 148 (FIG. 14) against the respective slide support tab 112 and tipping the slide support 206. When solenoid valve 412 returns to the vent position, the air cylinder 278 communicates with atmosphere, permitting the air cylinder 278 to return to its resting position. Tipper tip 148 then rises to its resting position, allowing the slide support to also return to its horizontal position. Three way solenoid valves 416 and 420 operate in an identical way, providing communication between the air inlet lines 414 and 418 and the respective air cylinders 280 and 282 when in the open position and actuating respective tipper tips 284 and 286. They also open communication between the air cylinders 280 and 282 and the atmosphere in the vent position, allowing the tipper tips to return to their elevated position.

Branch line 422 leads from line 408 to the reagent dispenser three way control solenoid valve 424. When energized to an "open" position, solenoid valve 424 permits pressurized air to pass from line 422 to air cylinder input line 300, causing rod 302 and foot 306 (FIG. 15) to press the reagent dispenser bottle 12 downward, emitting a precise volume of reagent liquid. When solenoid valve 424 is in the vent position, the air cylinder 18 and the reagent bottle 12 return to their resting positions.

Branch line 426 leads from line 403 to branched lines 428 and 430. Branch line 428 leads to pressure regulator 38, providing an output pressure of 10 psi in output line 431. Three way solenoid valve 432, when in the open position, provides communication between air input line 431 to the evaporation inhibitor liquid reservoir container 434 through lines 436 and 438. It also delivers pressurized air to the rinse liquid supply container 44 through line 440, rinse solution reservoir 441 and supply conduit 443. When solenoid valve is opened to atmosphere (vent position), air in line 436 and in containers 44 and 434 is bled or vented to the atmosphere. This permits removal, opening or replacement of reservoir container 434, or opening or removal of supply container 441. The pressured air in containers 434 and 441 forces liquid through respective output conduits 442 and 443.

Conduit 442 leads to two way solenoid valve 446, which has an outlet conduit 448 leading to the evaporation inhibitor application block 212 and associated nozzles. When the solenoid 446 is opened, evaporation inhibitor liquid is emitted from nozzles 294 (FIG. 14 and 15) onto the surface of the respective slide 234.

Conduit 444 delivers pressurized rinse liquid from heated rinse liquid container 44 to branch conduits 450, 452 and 454 leading to conventional rinse liquid two way solenoid valves 460, 462 and 464. When the solenoid valves 460, 462 and 464 are opened, pressurized rinse liquid is delivered to the respective rinse blocks 200, 202 and 204 through supply conduits 260, 268 and 276. The pressurized rinse liquid is emitted by the rinse blocks onto the slides positioned in the respective station (FIG. 13).

Branch line 430 leads to pressure regulator 64, providing an output pressure of 15 psi in output conduit 466 leading to vortex mixer air control two way solenoid valve 468. When in the open position solenoid valve 468 delivers pressurized air to output conduit 470 connected thereto. Conduit 470 leads to branch lines 472 and 474 leading to vortex mixing blocks 222 and 224. The pressurized air is emitted by nozzles 351 and 355 (FIG. 17), stirring the reagent layer on the respective slides 234.

Figure 23:
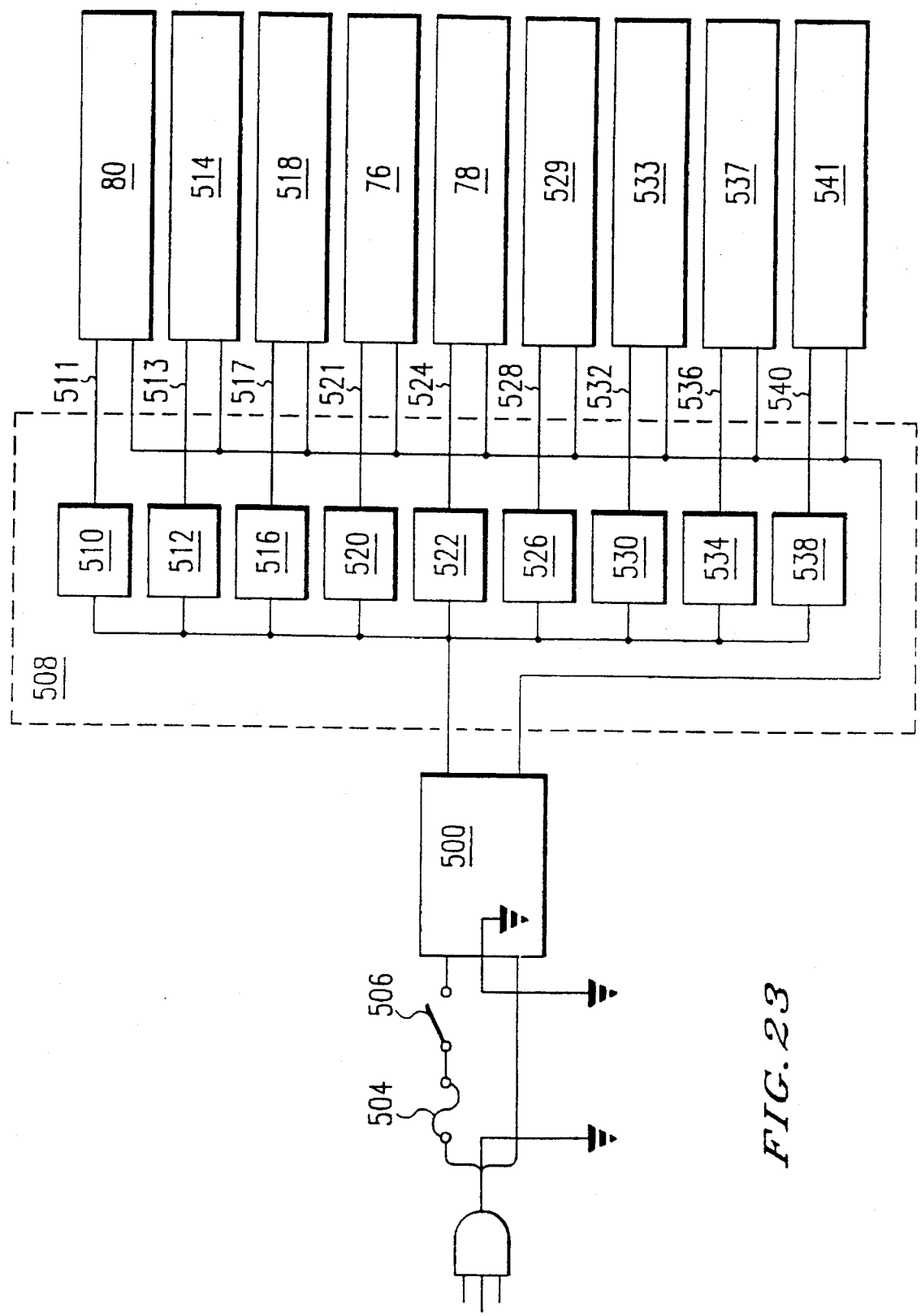
FIG. 23 is a schematic drawing of the 120 volt AC power distribution in the apparatus of this invention.

FIG. 23 is a schematic drawing of the 120 volt AC power distribution in the apparatus of this invention. The power circuit to power line filter 500 includes a main fuse 504 and main power switch 506. 120 Volt AC power to the air compressor 80 is provided by line 511 from the line fuse 510 in the I/O board 508. 120 Volt AC power to the air compressor cooling fan 514 is provided by line 513 from line fuse 512 in the I/O board 508. 120 Volt AC power to the electronics cooling fan 518 is provided by line 517 from line fuse 516 in the I/O board 508. 120 Volt AC power to the 24 volt DC power supply 76 is provided by line 521 from line fuse 520 in the I/O board 508. 120 Volt AC power to the 5 volt/12 volt DC power supply 78 is provided by line 524 from line fuse 522 in the I/O board 508. 120 Volt AC power to the computer card rack 529 is provided by line 528 from line fuse 526 in the I/O board 508. 120 Volt AC power to slide heater fan relay 533 is provided by line 532 from line fuse 530 in the I/O board 508. 120 Volt AC power to the slide heater relays 537 is provided by line 536 from fuse 534 in the I/O board 508. 120 Volt AC power to the rinse fluid heater relay 541 is provided by line 540 from fuse 538.

Figure 24:
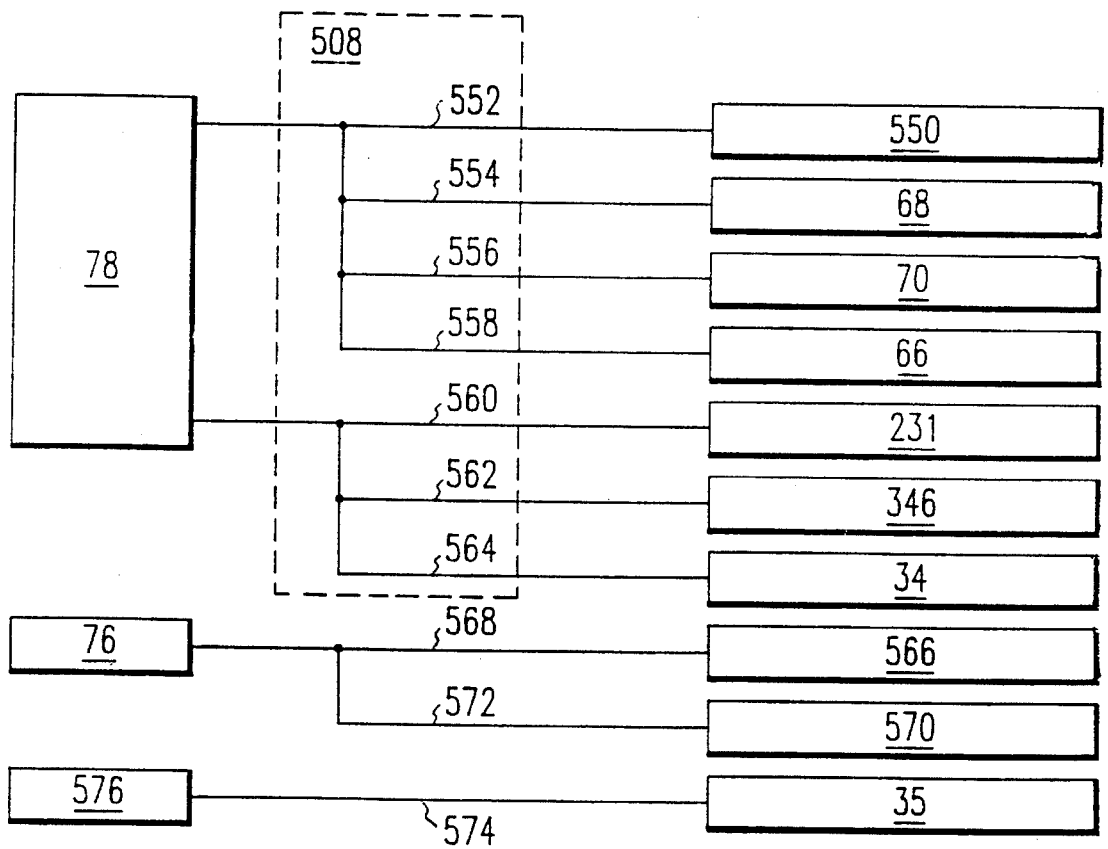
FIG. 24 is a schematic drawing of the DC power distribution in the apparatus of this invention.

FIG. 24 is a schematic drawing of the DC power distribution in the apparatus of this invention. 12 Volt DC logic power for printer 550 is provided by line 552 from the power supply 78. Similarly, 12 volt DC power for low slide temperature controller 68 is provided by line 554, 12 volt power for high slide temperature controller 70 is provided by line 556, and 12 volt power for rinse fluid temperature controller 66 is provided by line 558. 5 Volt DC laser power for the slide bar code reader 231 is provided by line 560 from the power supply 78, and 5 volt power for the laser of reagent bar code reader 346 is provided by line 562. 5 Volt DC power to the liquid crystal display 34 is provided by line 564.

24 Volt DC power is provided to the upper motor controller 566 for the stepper motor 14 by line 568. 24 Volt DC power for the lower motor controller 570 for the stepper motor 48 is provided from power supply 76 by line 572.

The conventional card rack 529 has a separate 5 volt/12 volt power supply 576. 5 Volt DC logic power and 12 volt DC motor power is provided to the floppy disc drive by lines 574.

Figure 25:
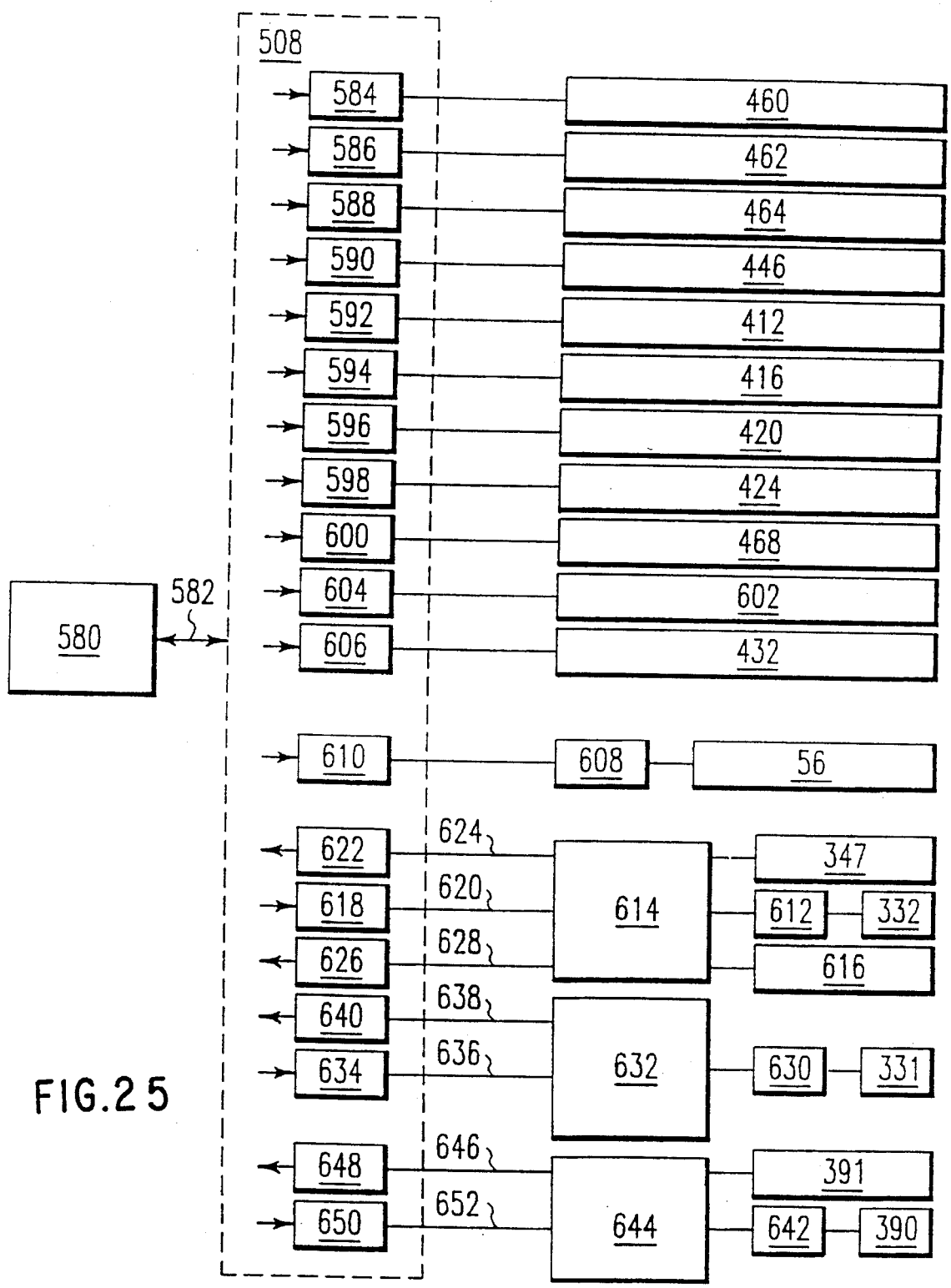
FIG. 25 is a schematic drawing of a first portion of the computer digital I/O system in the apparatus of this invention.

FIG. 25 is a schematic drawing of a first portion of the computer digital I/O system in the apparatus of this invention. The control system uses a series of standard optical relays, each of which are connected to close the line to ground in the power circuit for the respective component. The optical relays provide isolation.

Communication between the optical relays and the computer digital I/O board 580 is provided by lines 582. The two way solenoid valves 460, 462 and 464 controlling the rinse liquid flow from heated rinse supply 44 to the respective rinse blocks 200, 202 and 204 are energized to an open position and de-energized to a closed position by output signals from the computer digital I/O board 580 to the optical relays 584, 586 and 588. The two way solenoid valve 446 controlling the flow of evaporation control liquid from container 434 to the nozzle block 212 is energized to an open position or de-energized to a closed position by output signals from board 580 to optical relay 590.

The three way solenoid valves 412, 416 and 420 controlling air flow to the respective tipper air cylinders 278, 280 and 282 are energized to an open position (causing air flow) or de-energized to a closed position (venting cylinder air to the atmosphere) by output signals from computer I/O board 580 to respective optical relays 592, 594 and 596. The three way solenoid valve 424 controlling air flow to the micro delivery reagent dispenser control cylinder 300 is energized to an open position (causing air flow and reagent delivery) or de-energized to a closed position (venting cylinder air to the atmosphere) by output signals from computer I/O board 580 to respective optical relay 598. The two way solenoid valve 468 controlling air flow to the vortex air mixer blocks 220, 222 and 224 (FIG. 17) is energized to an open position (causing air flow to the mixer blocks) or de-energized to a closed position by output signals from computer I/O board 580 to respective optical relay 600.

The sound alarm 602 is activated to produce sound by an output signal from the computer I/O board 580 to optical relay 604. The sound alarm 602 can be activated to sound a 'beep' by keyboard key operation, by a longer 'beep' or double 'beep' at the completion of a run, and a sustained sound during a system malfunction, for example. The three way solenoid valve 432 controlling air flow to the rinse liquid and evaporation control liquid supply containers 44 and 434 (FIG. 22) is energized to an open position (causing air flow and pressurization of the supply containers) or de-energized to a closed position (venting cylinder air from the containers to the atmosphere) by output signals from computer I/O board 580 to respective optical relay 606.

The slide heat fan 56 speed is operated by pulse width modulation, that is, power pulses from the power relay 608. The fan 56 is energized by an output signal to the power relay 608 from optical relay 610. The timed signal to the optical relay 610 is received from the computer I/O board 580. The pulse width and speed of the fan 56 is adjusted in response to heating requests from the high temperature slide controller 632 to increase the volume of heating air delivered to the air distribution manifold 30.

The slide heater system control supplies separately controlled power to each of the resistance heating elements 331 and 332. Low temperature heating element 332 is energized by power relay 612 upon a signal from the low slide temperature controller 614. Thermistor 347 provides temperature information to the controller 614. During the operation of the apparatus at the lower temperatures required for the immunohistological processes, the power to the heating element 332 is turned on when operating heat is required, in response to a low temperature signal from the low temperature controller 614. It is turned off when the operating temperature is restored. The controller 614 also detects when the slide door switch 616 is closed. If the cabinet slide door is open, energy supply to the heating element 331 and 332 is interrupted. The heating cycle is initiated by a request for heat passed to the computer I/O board 580 through line 624 to the optical relay 622. The computer then responds with a heating power select heat signal received by controller 614 through line 620 from optical relay 618 in response to an output signal from the computer I/O board 580. A status signal for the slide door switch is received by the computer I/O board through line 628 and optical relay 626.

The high temperature heating element 331 is energized by power relay 630 upon a signal from the high slide temperature controller 632, in response to a power command signal through optical relay 634 and line 636 from the computer digital I/O board 580. During the operation of the apparatus at the lower temperatures required for the immunohistological processes, the power to the heating element 331 is turned on only during an initial warm-up cycle. During the warm-up cycle, heat energy is requested from the I/O board 580 through line 638 and optical relay 640.

When the apparatus is operated at the higher temperatures required for in situ hybridization, the heating elements are energized in a different control sequence by the controllers 614 and 632. As with the low temperature operation, both heating elements 331 and 332 are energized during the warm-up cycle. However, in the high temperature operating mode, the low temperature heating element 332 is continuously energized, and energy is supplied intermittently to the heating element 331. In the high temperature mode, therefore, the optical relay 634 receives a power command signal from the I/O output board 580 when the high temperature controller 632 signals that more heat is required. In addition to the heater controls described above, an additional thermostat is provided in the heater circuit which turns the heater off if the heater temperature reaches 160° C., for example if the fan 56 fails.

The rinse liquid heating system resistance heater 390 (FIG. 19) is energized through power relay 642 upon a signal from rinse fluid controller 644. Thermistor 391 monitors the rinse fluid temperature, and the controller 644 provides a signal indicating whether or not further heat energy is required. A heat request signal for heating liquid is received by the computer I/O board through line 646 and optical relay 648. The computer responds with a heat select signal from the I/O board 680 through relay 650 and line 652.

Figure 26:
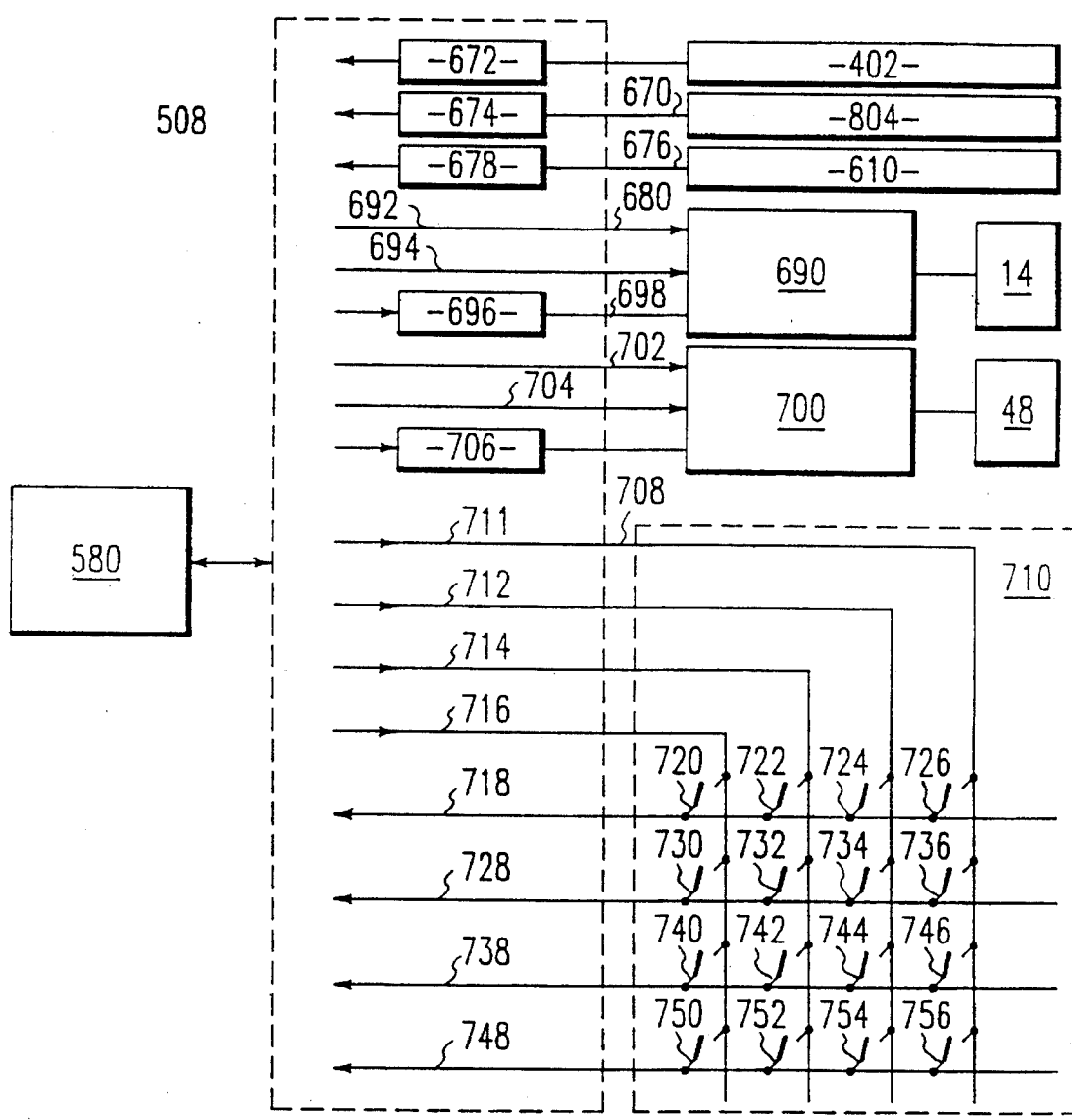
FIG. 26 is a schematic drawing of a second portion of the computer digital I/O system in the apparatus of this invention.

FIG. 26 is a schematic drawing of a second portion of the computer digital I/O system in the apparatus of this invention. The computer digital I/O board 580 receives a signal indicating closure of the air pressure switch 402 (FIG. 22) through line 670 and optical relay 672. The computer digital I/O board 580 receives a home signal from the reagent carousel metal proximity home sensor through line 676 and optical relay 674 when the metal block 803 and the reagent carousel 10 are in the home position. The computer digital I/O board 580 receives a home signal from the slide support metal proximity home sensor 610 through line 680 and optical relay 678 when the metal block 229 and the slide support carousel 24 are in the home position.

The reagent carousel stepper motor 14 is operated by reagent carousel stepper motor controller 690 in response to commands received from the computer digital I/O board 80. Command signals for steps (motor operation) are received through line 692, and command signals for the direction of operation are received through line 694. The stepper motor has a high and low torque operating mode, the low torque mode being effected by switching a resistor into the control circuit. The high torque mode is used to move the motor through the number of steps required to place a selected reagent bottle in the reagent delivery station. The low torque mode is used as a brake to hold the reagent bottle carousel in a position. The low or high torque command signal is received by the reagent carousel stepper motor controller 690 through line 698 and optical relay 696.

The slide support carousel stepper motor 48 is operated by slide support carousel stepper motor controller 700 in response to commands received from the computer digital I/O board 580. Command signals for steps (motor operation) are received through line 702, and command signals for the direction of operation are received through line 704. This stepper motor also has a high and low torque operating mode, activated in the same way and having the same functions as the reagent carousel stepper motor operating modes. The high torque mode is used to move the motor through the number of steps required to place a selected slide in a selected treatment zone. The low or high torque command signal is received by the slide support carousel stepper motor controller 700 through line 708 and optical relay 706. When the door switch 616 shows an open door status, the step command signals to the stepper motors 14 and 48 are prevented. If the door switch 616 is opened during a biological processing run, any incomplete stepper motor sequence is permitted to reach completion before further step command signals are blocked.

The keyboard 710 is a conventional pressure sensitive keyboard. The switches 720–726, 730–736, 740–746 and 750–756 are closed by manual pressure applied to the surface of an impermeable flexible plastic layer over the switches. The switches are isolated and protected under the plastic layer and are not fouled by moisture or debris from the laboratory or operator.

In operation input lines 711, 712, 714 and 716 are each sequentially energized for a brief period by the computer digital I/O board 580, and the lines 718, 728, 738 and 748 are each sequentially polled during this brief period. If line 718 polls positive while line 716 is energized, closure of switch 720 is indicated. In a similar manner, closure of switch 722 is indicated by a positive poll of line 718 when line 714 is energized, closure of switch 724 is indicated by a positive poll of line 718 when line 712 is energized, closure of switch 726 is indicated by a positive poll of line 718 when line 711 is energized, and the like.

Figure 27:
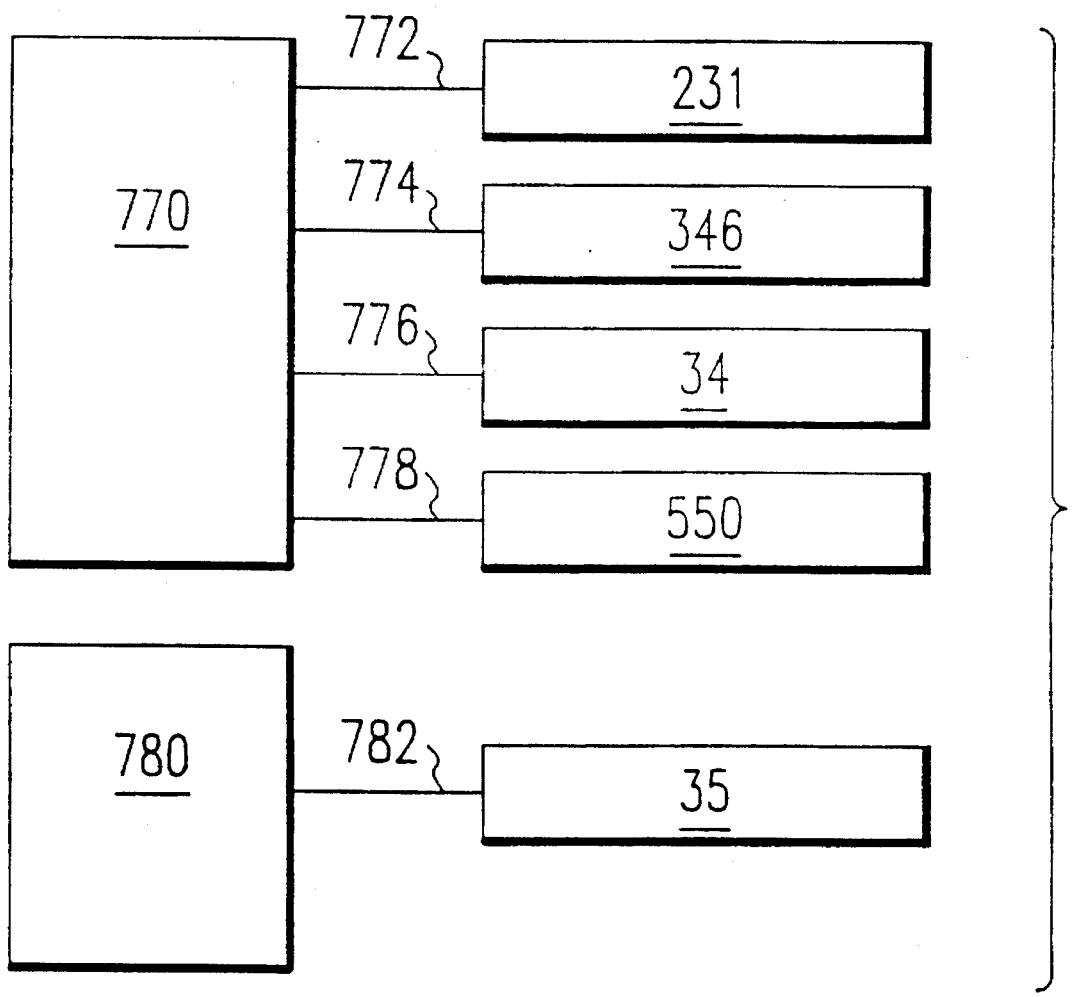
FIG. 27 is schematic drawing of the computer serial and floppy disk I/O system in the apparatus of this invention.

FIG. 27 is schematic drawing of the computer serial and floppy disk I/O system in the apparatus of this invention. The computer RS-232 I/O port 770 sends polling signal to the slide barcode reader 231 and receives signals indicating bar code information read through line 772. Similarly, the computer RS-232 I/O port 770 sends polling signal to the reagent carousel barcode reader 346 and receives signals indicating barcode information read through line 774. Signals to the liquid crystal display 34 are sent through line 776 from the RS-232 I/O port 770. The computer RS-232 I/O port 770 receives an availability polling signal from the printer 550 and sends digital data to printer 550 through line 778.

Immunohistological methods for which the apparatus of this invention are particularly suitable are described in concurrently filed, commonly assigned patent application Ser. No. 07/488,348 filed Mar. 2, 1990 (Attorney Docket No. 193.0007), the entire contents of which are hereby incorporated by reference. A typical immunohistological method, as carried out with the apparatus of this invention includes the following steps.

1) Preparing the slides, including applying a bar code to the slide indicating the immunohistological process to be used with the sample, and manually rinsing and applying evaporation inhibiting liquid to the tissue sample surface before placement in the apparatus to prevent dehydration of the sample.

2) Inserting a batch of slides in the apparatus, mounting each slide in a slide support.

3) closing the apparatus and beginning the treatment processing. The apparatus heating system is in the warm-up mode until the heating air temperature reaches the desired level.

4) A slide is rinsed in the first rinse station (FIG. 1114) in Seven rinse cycles. Each cycle includes applying a 500 μL pulse of rinse liquid followed by tipping the slide support to effect draining. This sequence can be repeated for seven rinse cycles as the slide is moved to and pauses in each of the second and third rinse stations, for a total of twenty-one rinse cycles, for example. The slide then is treated in a seven second stay in the evaporation inhibitor and reagent solution application station (FIGS. 11, 14 and 15). An initial quantity of 500 μL of an evaporation inhibiting liquid such as dodecane is applied to the slide surface. Then 200 μL of reagent solution is applied to the slide.

As each slide poises in the reagent application zone, the appropriate reagent container is moved by the reagent carousel to the reagent application station, and a metered volume of reagent is applied to the slide. In being applied to the slide, the reagent liquid is applied to the uppermost surface (the evaporation liquid layer). It then passes through the evaporation inhibiting liquid layer to the underlying aqueous layer, a procedure which would not be possible with a conventional solid glass coverslip.

6) The slide is then passed to each of the vortex mixing stations (FIGS. 11, 14, 16 and 17). Here vortex jets stir the reagent on the slide surface under the file of evaporation inhibiting liquid. This procedure would not be possible with a conventional solid glass coverslip.

7) The slide is then carried by the carousel, pausing as each slide support is sequenced through the same steps, until it returns to the initial rinse station, where the cycle is repeated. The reaction between the reagent and the tissue sample continues during this period, and slides in each of the following slide supports is subjected to the same sequence of rinse, application of evaporation inhibitor, application of reagent, stirring, and incubation.

8) In a typical immunohistological process using a four phase process with a peroxidase enzyme antibody label, a sequence total of five different reagents are applied as the tissue sample is passed five times through the reagent application zone. In such a process, the first reagent is a hydrogen peroxide solution required to eliminate endogenous peroxidase activity in the tissue sample. The second reagent is a primary antibody which binds selectively with an specific epitope for which the sample is being tested. The third reagent is a biotin labeled secondary antibody which binds preferentially with the primary antibody remaining on the sample following the preceding incubation and rinsing. The fourth reagent is avidin labeled with an enzyme such as a peroxidase enzyme, the avidin binding with the biotin label remaining on the sample following the preceding incubation and rinsing. The fifth reagent is a substrate solution which is converted by the peroxidase enzyme to form a detectable label such as a fluorophore or chromophore at the site of any primary antibody binding with the sample.

Figure 28:
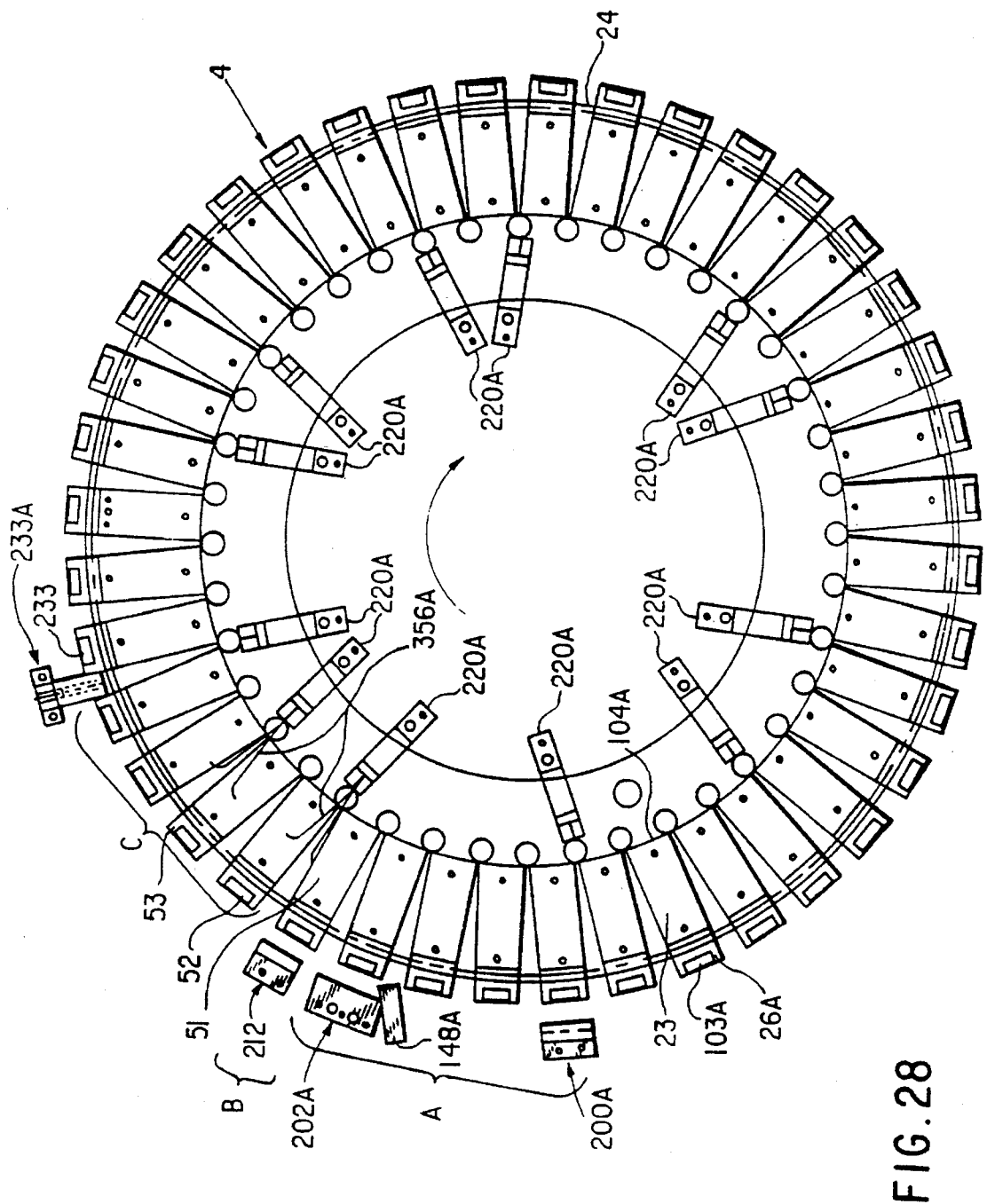
FIG. 28 is a further embodiment of the intermediate section of the apparatus of this invention which dispenses with the tipper rinse method.

9) Following the conclusion of the substrate solution treatment and incubation, the slide typically is removed from the carousel, coverslipped with a glass coverslip and examined to determine the extent of primary antibody binding with the tissue sample. FIG. 28 illustrates an alternative embodiment of the intermediate section 4, including the slide support carousel 24 and the associated slide treatment stations, which dispenses with the tipper rinse method described above and employs an alternative rinsing arrangement, using stationary slide supports, as will be more fully described hereinafter. The carousel 24 is rotated, for example, in a clockwise manner, as indicated by the arrow shown in FIG. 28, so that each slide support 26A and associated slide 234 is positioned in the rinse zone A, evaporator inhibitor and reagent application zone B, and agitation zone C for successive treatment and incubation as previously described above.

Figure 29A:
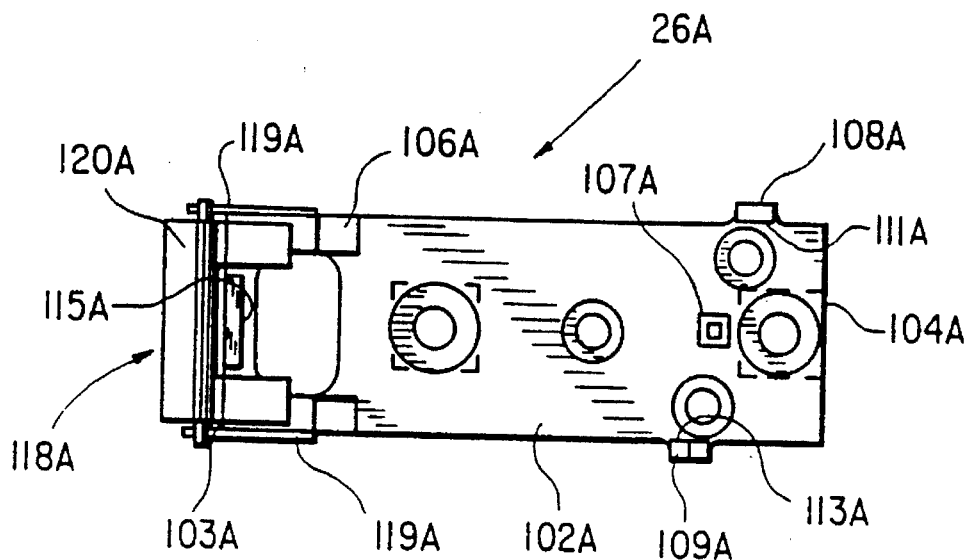
FIGS. 29A–29B are top and side views respective an alternative embodiment of the slide support for use with the embodiment of FIG. 28.
Figure 29B:
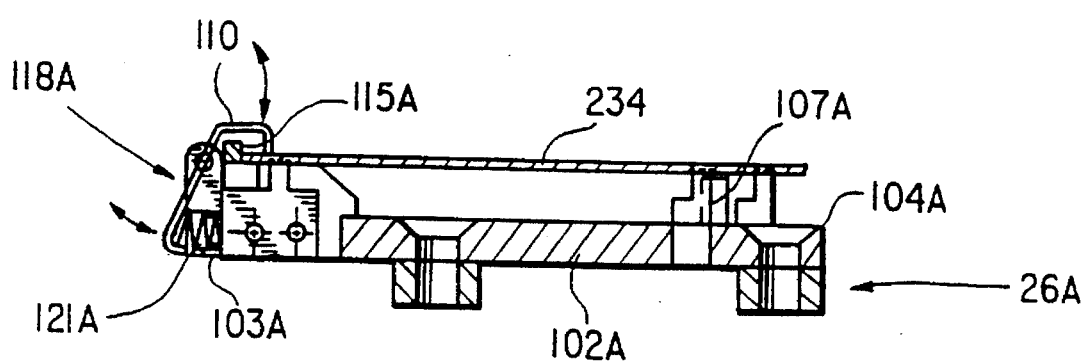

In the embodiment depicted by FIG. 28, an alterative embodiment of the slide support 26A is provided which does not pivot, but rather is fixedly supported in a predetermined position on the carousel 24 by screws or the like and structured so that the associated slide 234 is held substantially horizontally as best seen in FIGS. 29A–29B. Referring to FIGS. 29A–29B, the slide support 26A has a distal end 103A, which is juxtaposed to the center of the carousel 24, and a proximal end 104, which is positioned adjacent to an outer circumference of the carousel 24.

The support 26A comprises a support plate 102A having a raised terminal guide end platform 106, adjacent the proximal end 104A and a support post 107A, adjacent the distal end 103A. The platform 106A and the post 107A cooperate to support the slide 234 in a substantially horizontal position at a predetermined vertical distance with respect to raised terminal guide tabs 108A and 109A between which the slide 234 is positioned.

As best seen in FIG. 29B, the tabs 108A, 109A are provided with a vertical length such that the upper surface of the slide 234 is positioned above the upper ends of the guide tabs 108A, 109A while the respective lateral edges 111A, 113A of the tabs 108A, 109A engage the lateral sides of the slide 234, i.e., the tabs 108A and 109A do not extend as far as the upper surface of the slide 234 to prevent wicking-off of any liquid on the upper surface of the slide 234 by the tabs 108A and 109A. The lateral edges 111A, 113A cooperate with the a guide edge 115A at the platform 106A to orient the slide 234 at a predetermined position with respect to the slide support 26A, and thus the carousel 24, for treatment at the various treatment stations to be describe hereinafter.

A clamping arrangement, generally indicated at 118A, positioned at the proximal end 104A, clamps the slide 234 to the slide support 26A. The clamping arrangement comprises a pair of supports 119A between which a slide engaging member 120A is pivotally supported. Spring 121A biases the slide engaging member 120A to firmly hold the slide 234 against the platform 106A and post 107A. The slide support 26A permits easy loading and unloading of the slide 234, firmly holds the slide 234 in place, does not interfere with the operation of the bar code reader and prevents or minimizes the wicking, i.e., surface tension, from draining liquids off the slide 234.

An alternative embodiment of the rinsing arrangement forming the rinse zone A is employed in the embodiment depicted by FIG. 28 which replaces the rinse blocks, and arrangement thereof, used with the tipper rinse method previously described with respect to FIG. 14. Referring to FIG. 28, the rinse zone A employs a first rinse block 200A, having a single wash block nozzle, as best seen in FIGS. 30A–30B, and a second rinse block 202A, having a dual wash block nozzle, as best seen in FIG. 31.

The first wash block 200A is preferably positioned at the beginning of the rinse zone A and the second wash block 202A is preferably positioned at the end of the rinse zone A so that the first and second wash blocks are spaced from one another. The first wash block 200A pulses streams of rinse liquid onto a slide upon entering the rinse zone A and due to the meniscus effect of the rinse liquid at the edges of the slide, builds up a layer of rinse liquid which remains on the slide. After a predetermined waiting period, set by the time it takes for the slide carousel to transport a slide between the first and second wash blocks 200A, 202A, the second wash block 202A uses pulsed streams of rinse liquid, alternately directed at one and then the other of the longitudinal edges of the slides, to knock or sweep the previously deposited layer of rinse liquid off of the slide.

The rinsing arrangement depicted in FIG. 28 rinses or washes the upper surface of the slides with streams or jets of pulsed rinsing liquid, for example, water, so that a low volume of rinsing liquid is used to provide a high degree of rinsing. Because the rinsing of the slides is a key limit to the sensitivity of the assays as background or noise is directly related to rinsing and sensitivity is the signal to noise ratio, the wash blocks 200A, 202A precede the application of the reagent and are a preferred feature of this embodiment of the invention.

Figure 30A:
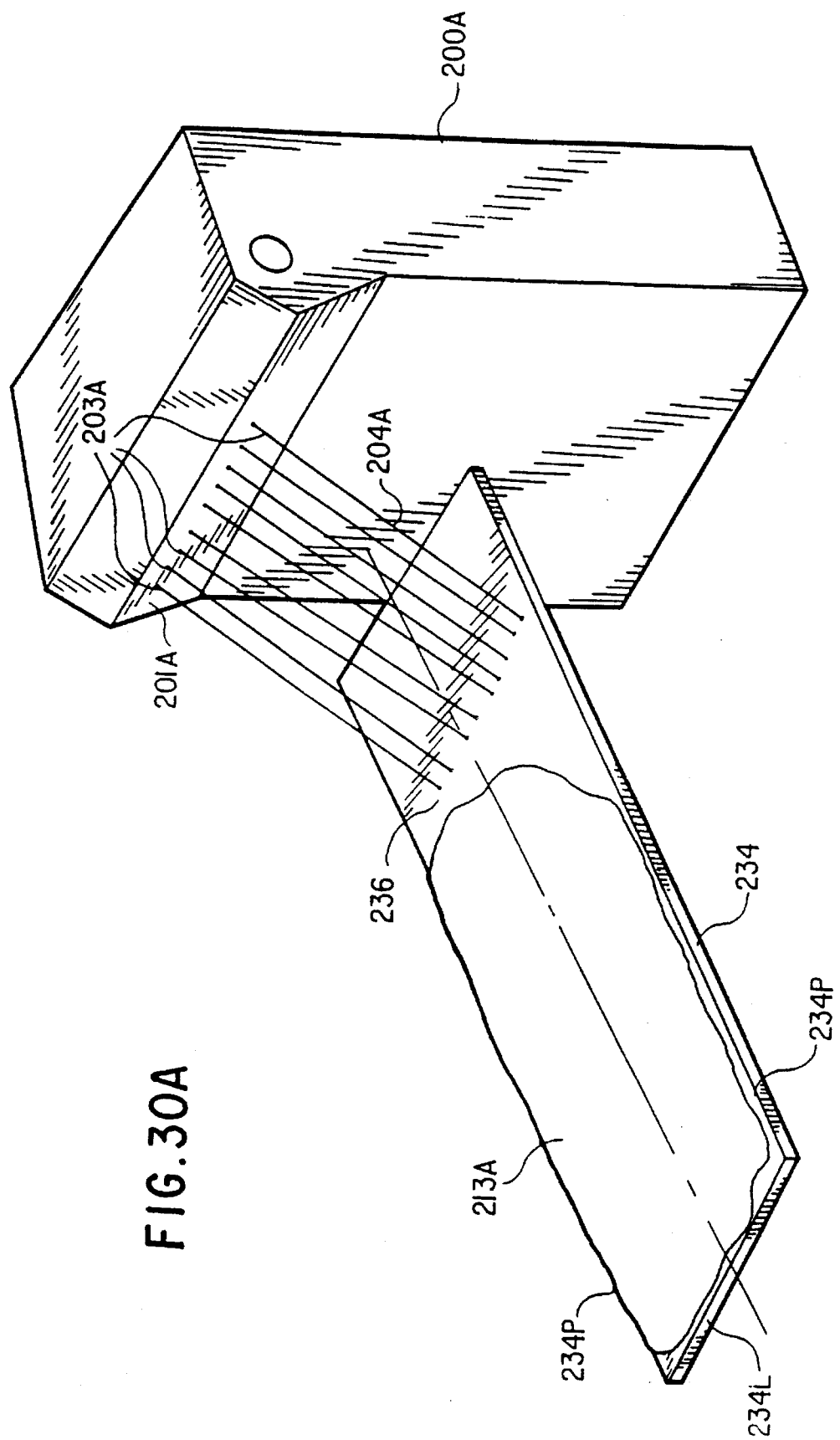
FIG. 30A is a side, isometric view of one embodiment of a single wash block nozzle for use with the embodiment of FIG. 28.
Figure 30B:
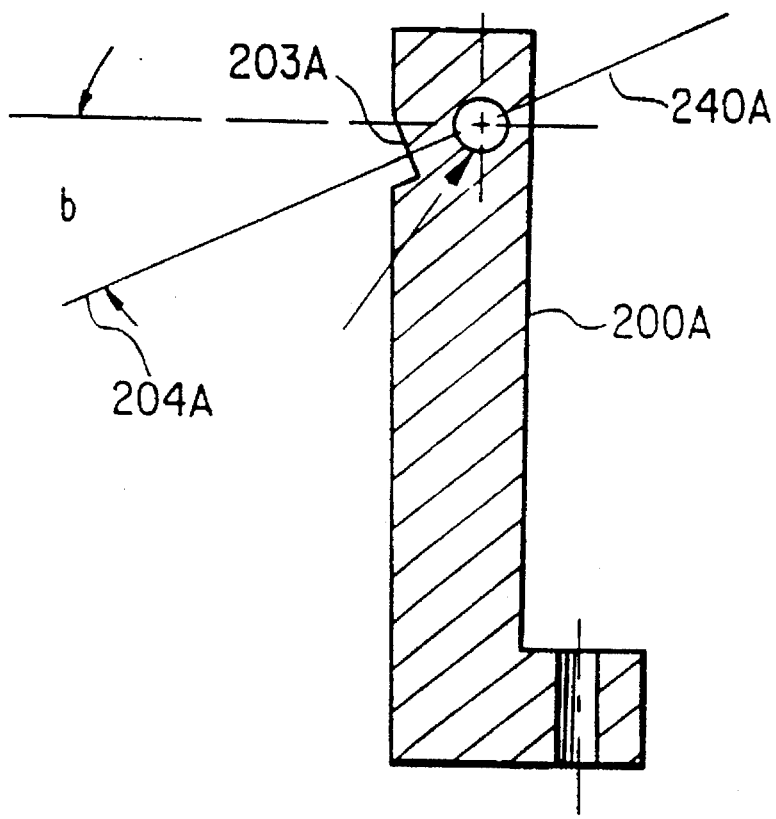
FIG. 30B is a side, cross-sectional view of the single wash block nozzle of FIG. 30A.
Figure 31:
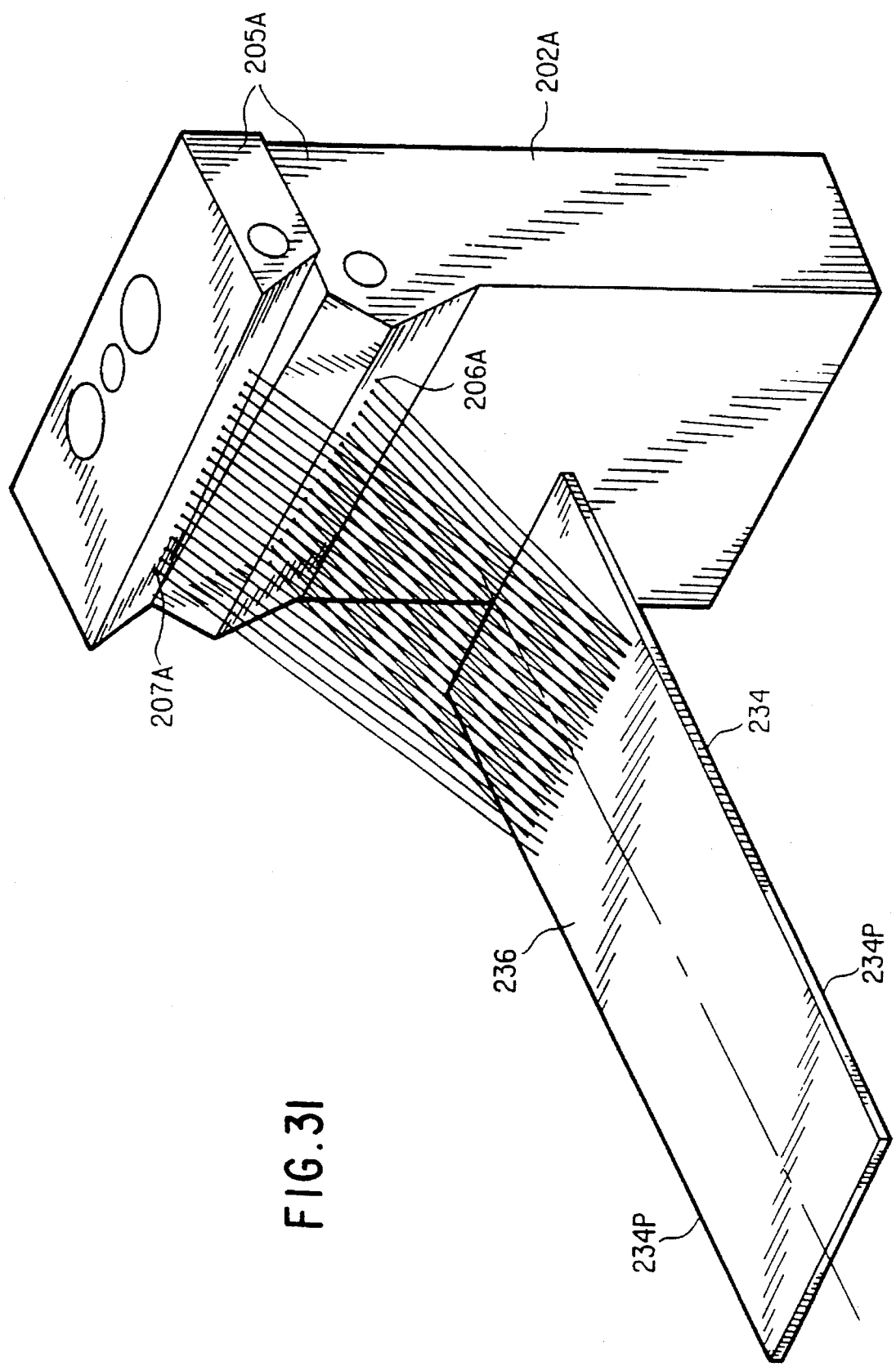
FIG. 31 is a side, isometric view of one embodiment of a dual wash block nozzle for use with the embodiment of FIG. 28.

Referring to FIG. 30A, the first wash block 200A comprises a single wash block nozzle 201A having a plurality of nozzle outlet openings 203A, for example 10 or so openings, which each provide a pulsed stream of rinse liquid 204A which impacts the rinse liquid impact zone 236 of the slide 234 as previously described. Due to the meniscus effect of the rinse liquid at the longitudinal edges 234P and lateral edge 234L of the slide 234, a layer of rinse liquid 213A is built up on the slide 234 as a result of the repeated pulsing of streams of rinse liquid during the operation of the first wash block 200A.

As best seen in FIG. 30B, a nozzle axis 240A of the nozzles of block 200A forms an angle b with the horizontal, this angle being between 15 and 35 degrees, preferably substantially 25 degrees.

FIG. 31 illustrates the second wash block 202A which employs a dual wash block nozzle 205A comprising a lower set of nozzle outlet openings 206A and an upper set of nozzle outlet openings 207A which respectively direct streams of pulsed rinse liquid towards one or the other of the longitudinal edges 234P of the slide 234.

As with the first wash block 200A, the streams of pulsed rinsing liquid, from each of the lower and upper sets of nozzle outlet openings 206A and 207A, preferably impact the slide 234 at the rinse liquid impact zone 236 which is upstream on the slide 234 from the tissue sample (not shown) positioned thereon. This feature of the first and second wash blocks 200A and 202A is important due to the fragile nature of the tissue sample positioned on the slide 234. By directing the streams of pulsed rinsing liquid at the impact zone 236 of the slide 234, the rinse liquid is provided with laminar flow by the time the rinse liquid reaches the tissue sample. As a result, undue damage to the fragile tissue sample is prevented.

The upper set of nozzle outlet openings 207A is constructed so that the associated streams of rinse liquid are off-set at an angle from the longitudinal center line of the slide 234 so that the pulsed streams of rinse liquid are directed toward one of the longitudinal edges 234P of the slide 234. The lower set of nozzle openings 206A is constructed so that the associated streams of rinsing liquid are also off-set at an angle from the longitudinal center line of the slide 234 so that the pulsed streams of rinse liquid are directed toward the other one of the longitudinal edges 234P of the slide 234. As a result of this arrangement, pulsed streams of rinse liquid are alternately and repeatedly directed to one and then the other of the longitudinal edges 234P of the slide 234 as will be more fully described hereinafter.

Preferably, separate plumbing and valving are provided for each of the lower and upper sets of nozzle outlet openings 206A and 207A of the dual wash block nozzle 205A to permit independent operation thereof. In operation, wash block 202A directs streams of pulsed rinsing liquid, for example from the lower set of nozzle openings 206A, toward a single longitudinal edge 234P of the slide 234 and after completion then directs streams of pulsed rinse liquid, for example from the upper set of nozzle opening 207A, to the other longitudinal edge 234P of the slide 234. This procedure is repeated and has the effect of sweeping or knocking the layer of rinse liquid 213A off of the slide 234.

As with the first wash block 200A, the nozzle axis 240 (not shown) of each of the upper and lower set of nozzle openings 207A, 206A forms an angle b (not shown) with the horizontal of between 15 and 35 degrees, preferably substantially 35 degrees for the upper set of openings 207A and substantially 25 degrees for the lower set of openings 206A.

Figure 32:
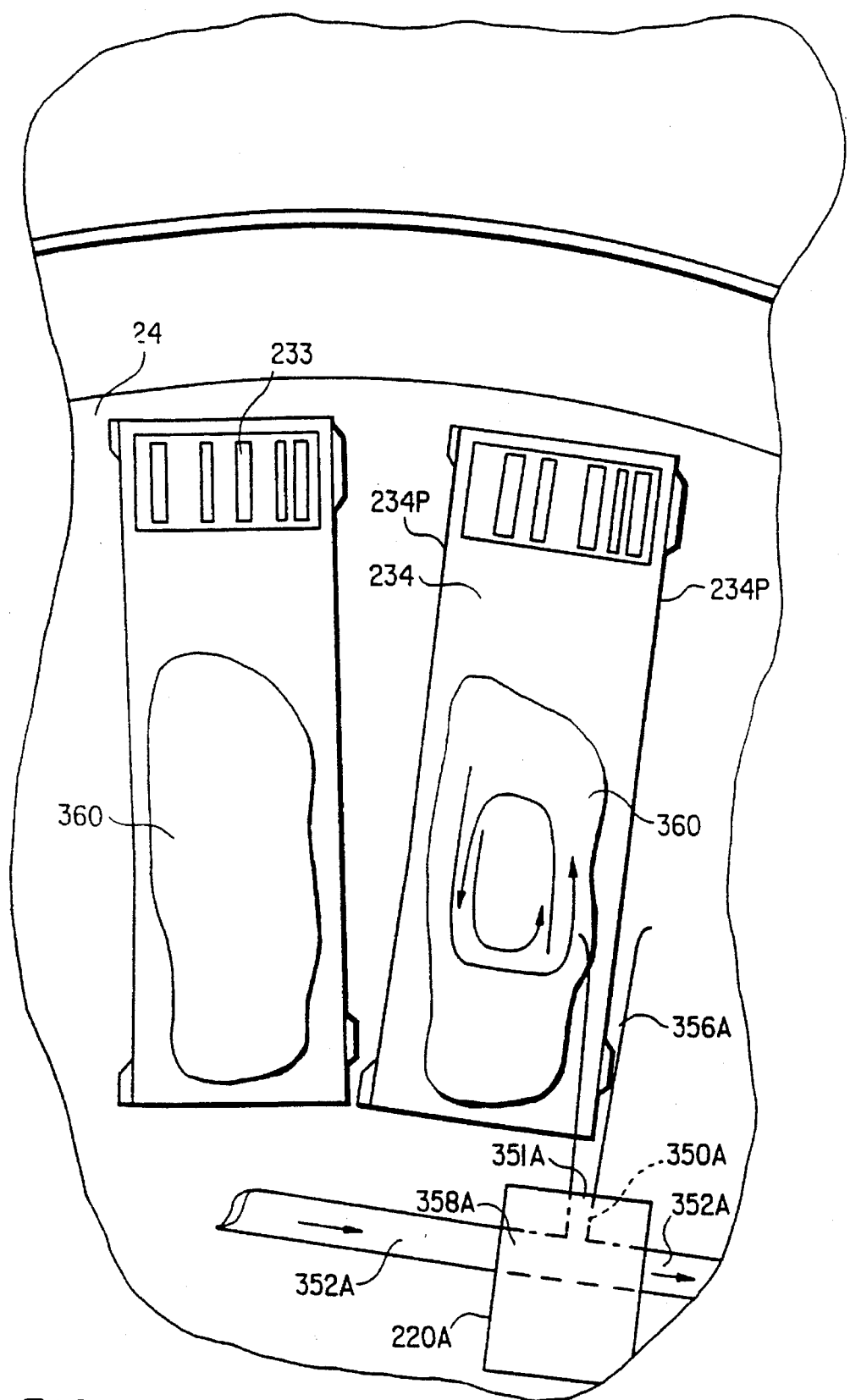
FIG. 32 is a top view of a further embodiment of the vortex mixers for use with the embodiment of FIG. 28.

FIG. 32 illustrates an alternative embodiment of a vortex air mixer 220A which in this case is a single mixer. Each of the single vortex air mixers 220A is positioned at the inner radius of the slides 234 such that an gas jet or cone 356A of, for example, air or the like, blows outwardly adjacent one of the longitudinal lateral edges 234P of the associated slide 234 to effect mixing in a manner similar to that described with respect to FIG. 17. More specifically, the gas stream 356A impacts the surface of the evaporation liquid surface layer 360 and moves the underlying reagent solution in a circular path on the tissue section.

Each vortex mixer 220A has a nozzle channel 350A, including a nozzle orifice 351A, which is supplied with pressurized air via a supply channel 358A, the nozzle channel 350A preferably intersecting the supply channel at a lower portion thereof. Pressurized air is supplied to the supply channel 358A from a air supply conduit 352A (arrows indicating the flow of air to and from the mixer 220A) connected to a pressurized air source (not shown). Each of the vortex mixers 220A can be supplied with pressurized air via a common supply conduit 352A which connects and supplies each of the supply channels 358A of the plurality of mixers 220A illustrated in FIG. 28.

As best seen in FIG. 28, there are, for example twelve, single vortex mixers 220A on the inner radius of the slides 234. The nozzle orifice 351A of each of the mixers 220A is preferable positioned so that the center of the gas jet or cone 356A is approximately 2 mm above the surface of the slide 234 and 4 mm in from the adjacent edge 234X of the slide 234 as best seen in FIG. 32.

A first mixer 220A is preferably positioned at station $2 adjacent the reagent drop point station S1 and a second mixer 220A is positioned at station S3, the mixers 220A at stations S2 and S3 directing the stream of air 356A to opposite longitudinal edges 234P of an associated slide 234 so that mixing is enhanced as described below.

The exact positioning of the remaining mixers 220A is not critical, these mixers 220A being positioned to provide a semi-continuous mixing. Additionally, each mixer 220A is spaced so that they alternate in blowing the right side and then the left side of the slide 234. That is, the even mixers blow up the right side of each slide 234 passing by and the odd mixers blow up the left side or vice versa. This enhances kinetic mixing, provides uniform coverage and averages out any possible temperature differences across each of the slides 234. These features lead to more rapid and reproducible staining than can be obtained manually.

Additionally, the intermediate section 4 of the embodiment of FIG. 28 is provided with a bar code cleaner, generally indicated at 233A, for cleaning drops of liquid off of the bar codes 233 (FIG. 32) provided for each of the slides 234 for identification purpose as previously described. It should be noted that the bar code cleaner 233A is equally applicable to the previously described embodiment of the invention employing the tipper rinse method described above. The bar code cleaner 233A is positioned, for example, downstream from the reagent drop point station S1 just beyond the first vortex agitation zone C as best seen in FIG. 28 and upstream and adjacent to the bar code reader position (not shown).

Figure 33A:
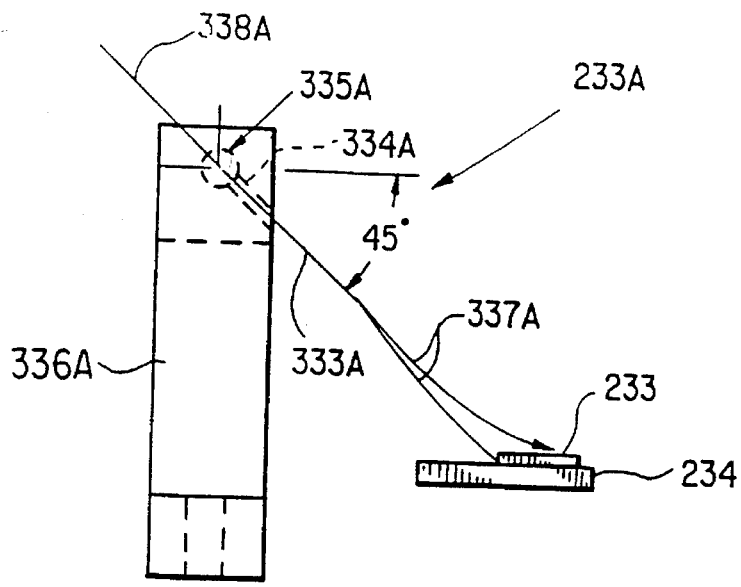
FIGS. 33A–33B are side and front views respectively of bar code cleaning arrangement for use with the embodiment of FIG. 28.
Figure 33B:
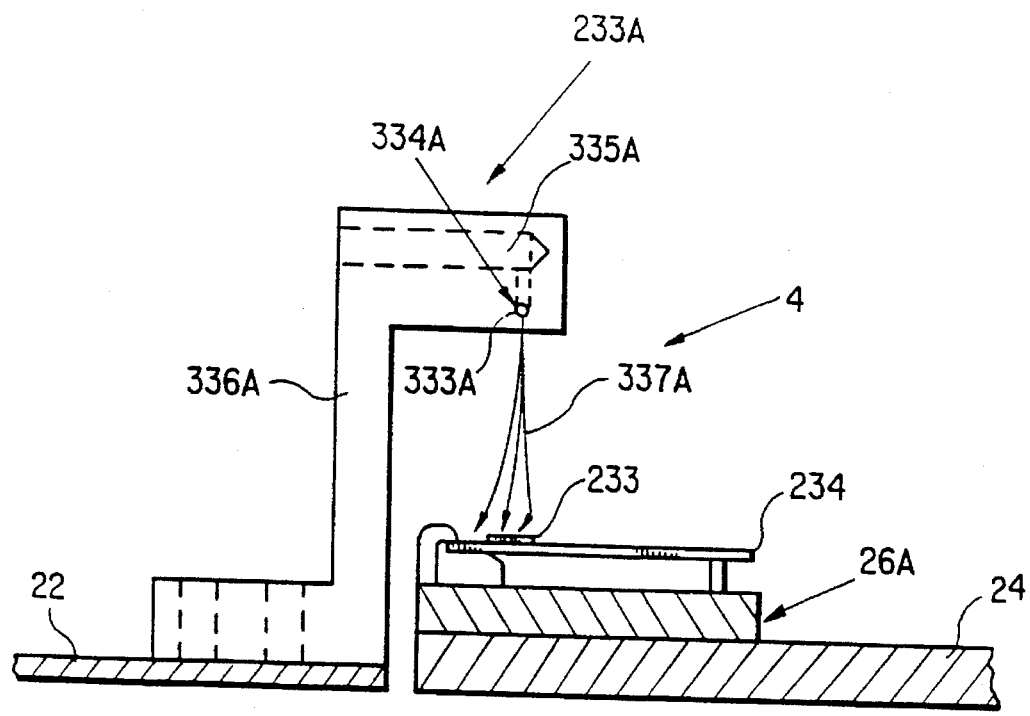

The bar code cleaner 223A is illustrated in detail in FIGS. 33A–33B and comprises a bar code nozzle 333A supplied with compressed air or the like via a supply channel 334A which is connected to a compressed air source (not shown) by supply conduit 335A. The bar code nozzle 333A is supported above the slide carousel 24 by support 336A, as best seen in FIG. 33B, and affixed to the stationary support plate 22 of the intermediate section 4. The nozzle 333A emits a stream or cone of air 337A which blows across the bar code 233 of an adjacent slide 234 attached to the associated slide support 26A. The stream of air 337A blows drops of liquid off of the bar code 233 which otherwise interfere with the reading of the bar codes by the bar code reader.

As best seen in FIG. 33A, the nozzle axis 338A of the bar code nozzle 333A forms an angle of about 45 degrees with the horizontal. Additionally, the stream of air 337A preferably strikes the bar code 233A in the area of the side of the bar code 233A closest to nozzle 333A.

Figure 34:
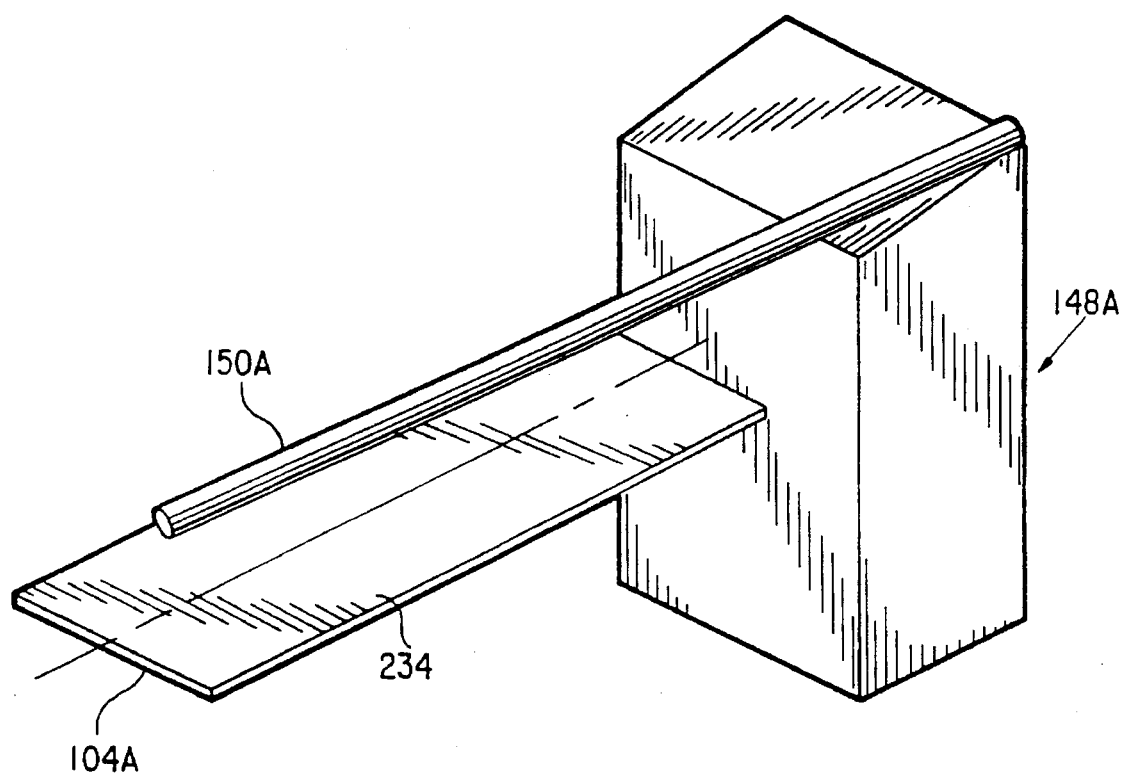
FIG. 34 is a side, isometric view of one embodiment of a jet drain for use with the embodiment of FIG. 28.

Since the embodiment of the intermediate section 4 described with reference to FIG. 28 does not employ the tipper rinse method, any rinse liquid remaining on the slide after operation of the second wash block 202A is drained from the upper surface of the slides 234 by a jet drain 148A which is illustrated schematically by FIG. 34. The preferred position of the jet drain 148A is at the last rinse station of the rinse zone A just prior to the reagent drop point station S1 as best seen in FIG. 28.

The jet drain 148A directs a fluid stream 150A of, for example air, at substantially a 45 degree angle to the longitudinal axis of an associated slide 234 and across one corner of the distal end 104A of the associated slide 234. The action of the fluid stream 150A acts to blow, aspirate or siphon the buffer remaining after the rinsing performed at the rinse zone A as described above.

Except for the differences noted above the embodiment so described with respect to FIG. 28 is the same as the apparatus described above in connection with the tipper rinse method and is capable of operating and performing the immunohistological methods as previously described.

We claim:

1. An automated biological reaction apparatus comprising:

a rotatable slide support carousel;

a plurality of slide supports mounted on the slide support carousel in a circular array for supporting a plurality of slides;

drive means engaging the slide support carousel for rotating the slide support carousel;

a reagent delivery system for applying a predetermined quantity of reagent to one of the slides on one of the slide supports positioned, by rotation of the slide support carousel, in a reagent delivery zone;

an evaporation inhibiting liquid application station comprising at least one nozzle positioned for directing a stream of evaporation inhibiting liquid onto a preselected evaporation inhibiting liquid impact zone of one of the slides on one of the slide supports;

a vortex mixing assembly positioned at a vortex agitation zone, the vortex mixing assembly having a nozzle for directing fluid at a vortex agitation zone of one of the slides on one of the slide supports and being positioned at the vortex agitation zone;

a heat zone for heating samples positioned on one of the slides on one of the slide supports;

at least one rinse station at a rinse zone, the rinse station comprising at least one nozzle positioned for directing a stream of rinse liquid onto a rinse liquid impact zone of one of the slides on one of the slide supports positioned at the rinse zone; and a draining means for draining rinse liquid from one of the slides on one of the slide supports.

2. The automated biological reaction apparatus of claim 1 wherein the reagent delivery system comprises a reagent carousel for supporting reagent containers and for positioning a selected reagent container at the reagent delivery zone, the reagent carousel being rotatably mounted above the slide support carousel.

3. The automated biological reaction apparatus of claim 2 wherein identification means are provided for identifying each reagent container supported by the reagent carousel and for identifying each slide supported by the slide support carousel.

4. The automated biological reaction apparatus of claim 1 wherein each of the slide supports on the slide support carousel has raised lateral guide tabs with guide termini between which one of the slides is positioned at a first end of the slide support, and a slide clamping arrangement for clamping one of the slides to the slide support, wherein the guide termini are lower than an upper surface of the slide.

5. The automated biological reaction apparatus of claim 4 wherein the vortex mixing assembly is positioned adjacent an inner circumference of the slide support carousel.

6. The automated biological reaction apparatus of claim 1 further including a bar code reader for reading bar codes on slides positioned on the slide supports.

7. The automated biological reaction apparatus of claim 6 further including a bar code cleaner for cleaning bar codes on the slides.

8. The automated biological reaction apparatus of claim 1 wherein the draining means comprises a jet drain for directing a fluid stream across an upper surface of one of the slides.

9. The automated biological reaction apparatus of claim 1 wherein the at least one rinse station comprises a first rinsing means at a beginning of the rinse zone and a second rinsing means at an end of the rinse zone.

10. The automated biological reaction apparatus of claim 9 wherein the first rinsing means includes at least one nozzle for depositing a layer of rinse liquid onto an upper surface of one of the slides, the slide being positioned at the beginning of the rinse zone, and the second rinsing means includes sweeping means for sweeping the layer of rinse liquid off of the slide when the slide reaches the end of the rinse zone.

11. The automated biological reaction apparatus of claim 10 wherein the first rinsing means and the second rinsing means are spaced from one another so that a predetermined period of time transpires during the transport of the slide between the first and second rinsing means before the layer of rinse liquid is swept off of the slide.

12. The automated biological reaction apparatus of claim 11 wherein the sweeping means of the second rinsing means comprises fluid pulsing means for forming pulsed streams of rinse liquid, alternately directed at one and then an other of longitudinal edges of the slides, to sweep the layer of rinse liquid off of the slide.

13. The automated biological reaction apparatus of claim 1 wherein the reagent delivery system comprises a reagent carousel having a plurality of reagent container supports thereon, the reagent carousel positioned above the slide support carousel for applying a predetermined volume of reagent to one of the slides on the slide support carousel in the reagent delivery zone.

14. The automated biological reaction apparatus of claim 13 further comprising homing and indexing means, operatively coupled to the reagent carousel, for identifying a position of each reagent container support with reference to a home position.

15. The automated biological reaction apparatus of claim 14 further comprising drive means, engaging the reagent carousel and operatively coupled to the homing and indexing means, for rotating the reagent carousel and positioning a preselected reagent container support in a reagent supply zone wherein the reagent supply zone is oriented so that a reagent in a container in the preselected reagent container support is dispensable directly from the reagent container to a sample on the slide.

16. The automated biological reaction apparatus of claim 1 wherein the at least one rinse station further comprises a rinse liquid application assembly including a heater for providing a rinse liquid having a temperature within a selected temperature range.

17. The automated biological reaction apparatus of claim 16 further comprising a delivery assembly, operatively coupled to the rinse liquid application assembly, for delivering liquid from the rinse liquid application assembly to the slide.

18. The automated biological reaction apparatus of claim 14 wherein the reagent carousel is rotatably mounted on a reagent carousel support and the homing and indexing means further comprises a proximity sensor and an object detectable by the proximity sensor when the proximity sensor and the object are in close proximity, one of the object and the proximity sensor being mounted on the reagent carousel, and the other of the object and the proximity sensor being mounted on the reagent carousel support in a position adjacent the path the other.

19. The automated biological reaction apparatus of claim 18 wherein the object is metallic and mounted on the reagent carousel and the proximity sensor is a metal proximity sensor mounted on the reagent carousel support.

20. The automated biological reaction apparatus of claim 15 wherein the reagent carousel is rotatably mounted on a reagent carousel support, the reagent carousel has a bar code zone, and the homing and indexing means further comprises a bar code reader mounted on the reagent carousel support in a position to read a bar code on a reagent container positioned in the bar code zone, whereby a bar code identifying a reagent contained in the reagent container in the preselected reagent container support can be read with reference to the home position by the bar code reader, and the reagent container containing the identified reagent can be automatically positioned in the reagent supply zone.

21. The automated biological reaction apparatus of claim 13 further comprising a reagent delivery actuator for engaging a reagent container positioned in the reagent delivery zone and for initiating delivery of a predetermined volume of reagent from the reagent container directly to the slide.

22. The automated biological reaction apparatus of claim 15 wherein the drive means engaging the reagent carousel comprises a stepper motor having a rotational mode for rotating the reagent carousel and a braking mode for resisting rotation of the reagent carousel.

23. The automated biological reaction apparatus of claim 13 wherein the reagent carousel includes a reagent support tray removably supported by a reagent tray support and the reagent support tray has indexing support feet on an underside thereof which are removably positioned in receptors in the reagent tray support such that the reagent support tray can be removed from the reagent tray support and replaced on the reagent tray support in the same indexed position.

24. The automated biological reaction apparatus of claim 16 wherein the rinse liquid application assembly further comprises:

a container for receiving liquid; and a temperature regulating device, operatively mounted on the container, for maintaining liquid in the container within the selected temperature range.

25. The automated biological reaction apparatus of claim 24 wherein the temperature regulating device further comprises:

a temperature sensor, operatively mounted on the container, for measuring liquid temperature, the temperature sensor generating a signal representing the liquid temperature; and a safety thermostat connected to the temperature regulating device for terminating a flow of power to the temperature regulating device if the temperature of the container exceeds a predetermined safety limit.

26. The automated biological reaction apparatus of claim 24 wherein the heater further comprises a heating jacket that contacts at least a portion of an outer surface of the container.

27. The automated biological reaction apparatus of claim 22 wherein the temperature regulating device further comprises a power supply, connected to the temperature sensor and to the heater, for energizing the heater when the temperature of the liquid is below a first pre-determined level and for de-energizing the heater when the temperature of the liquid is above a second pre-determined level, thereby maintaining the temperature of the liquid within the selected temperature range.

28. The automated biological reaction apparatus of claim 17 wherein the delivery assembly further comprises a sprayer assembly for spraying liquid onto a surface of the slide.

29. The automated biological reaction apparatus of claim 1 wherein the drive means engaging the slide support carousel comprises a stepper motor having a rotational mode for rotating the slide support carousel and a braking mode for resisting rotation of the slide support carousel.

* * * * *